(12) United States Patent
Ogawa

(10) Patent No.: US 8,864,477 B2
(45) Date of Patent: Oct. 21, 2014

(54) COMPRESSOR AND OXYGEN CONCENTRATOR

(75) Inventor: Hiroshi Ogawa, Sayama (JP)

(73) Assignee: Ikiken Co., Ltd., Sayama-Shi, Saitama (JP)

( * ) Notice: Subject to any disclaimer, the term of this patent is extended or adjusted under 35 U.S.C. 154(b) by 394 days.

(21) Appl. No.: 13/194,245

(22) Filed: Jul. 29, 2011

(65) Prior Publication Data

US 2012/0027628 A1 Feb. 2, 2012

(30) Foreign Application Priority Data

Jul. 30, 2010 (JP) ................................. 2010-172428

(51) Int. Cl.
*F04B 35/04* (2006.01)
*F04B 45/04* (2006.01)
*A61M 16/10* (2006.01)
*F04B 43/04* (2006.01)
*A61M 16/00* (2006.01)
*A61M 16/06* (2006.01)
*F04B 45/047* (2006.01)
*F04B 43/02* (2006.01)

(52) U.S. Cl.
CPC .............. *F04B 43/026* (2013.01); *F04B 45/04* (2013.01); *A61M 2202/0208* (2013.01); *A61M 16/10* (2013.01); *A61M 2205/502* (2013.01); *F04B 43/04* (2013.01); *A61M 2205/8262* (2013.01); *A61M 16/0057* (2013.01); *A61M 16/101* (2013.01); *A61M 16/0063* (2013.01); *A61M 16/0677* (2013.01); *A61M 2209/08* (2013.01); *F04B 45/047* (2013.01); *A61M 2016/1025* (2013.01); *A61M 2205/8206* (2013.01)
USPC .................. 417/423.14; 417/313; 128/205.24

(58) Field of Classification Search
USPC ............ 417/404, 418, 350, 415, 423.14, 478, 417/564; 128/205.11, 205.18, 205.24, 128/205.25, 205.29, 204.18
See application file for complete search history.

(56) References Cited

U.S. PATENT DOCUMENTS

| | | | | |
|---|---|---|---|---|
| 4,673,415 A | * | 6/1987 | Stanford | ............................ 95/19 |
| 5,484,268 A | * | 1/1996 | Swank | ........................... 417/211 |
| 6,651,658 B1 | | 11/2003 | Hill et al. | |
| 8,435,013 B2 | | 5/2013 | Kondou et al. | |
| 2002/0096174 A1 | | 7/2002 | Hill et al. | |
| 2002/0114706 A1 | * | 8/2002 | Bassine | ...................... 417/199.1 |
| 2005/0047947 A1 | * | 3/2005 | McCombs et al. | ............ 417/545 |
| 2005/0069431 A1 | * | 3/2005 | Leu | ................................ 417/415 |
| 2005/0112002 A1 | * | 5/2005 | Leu | ................................ 417/419 |
| 2006/0045768 A1 | | 3/2006 | Chuang | |
| 2007/0280838 A1 | * | 12/2007 | Otte et al. | ...................... 417/360 |

FOREIGN PATENT DOCUMENTS

| | | |
|---|---|---|
| JP | 2002-045424 A | 2/2002 |
| JP | 2008-274840 A | 11/2008 |
| WO | 2008/096874 A1 | 8/2008 |

* cited by examiner

*Primary Examiner* — Devon Kramer
*Assistant Examiner* — Amene Bayou
(74) *Attorney, Agent, or Firm* — Buchanan Ingersoll & Rooney PC

(57) ABSTRACT

A compressor that generates compressed air by compressing raw air has a case section; a driving motor that is provided in the case section and that has an output shaft; head sections operated by the rotation of the output shaft of the driving motor and that suck and compress raw air to generate thereby compressed air; and a raw air intake section formed of a plurality of raw air intake holes for taking raw air into the case section and supplying the raw air to the head sections.

17 Claims, 14 Drawing Sheets

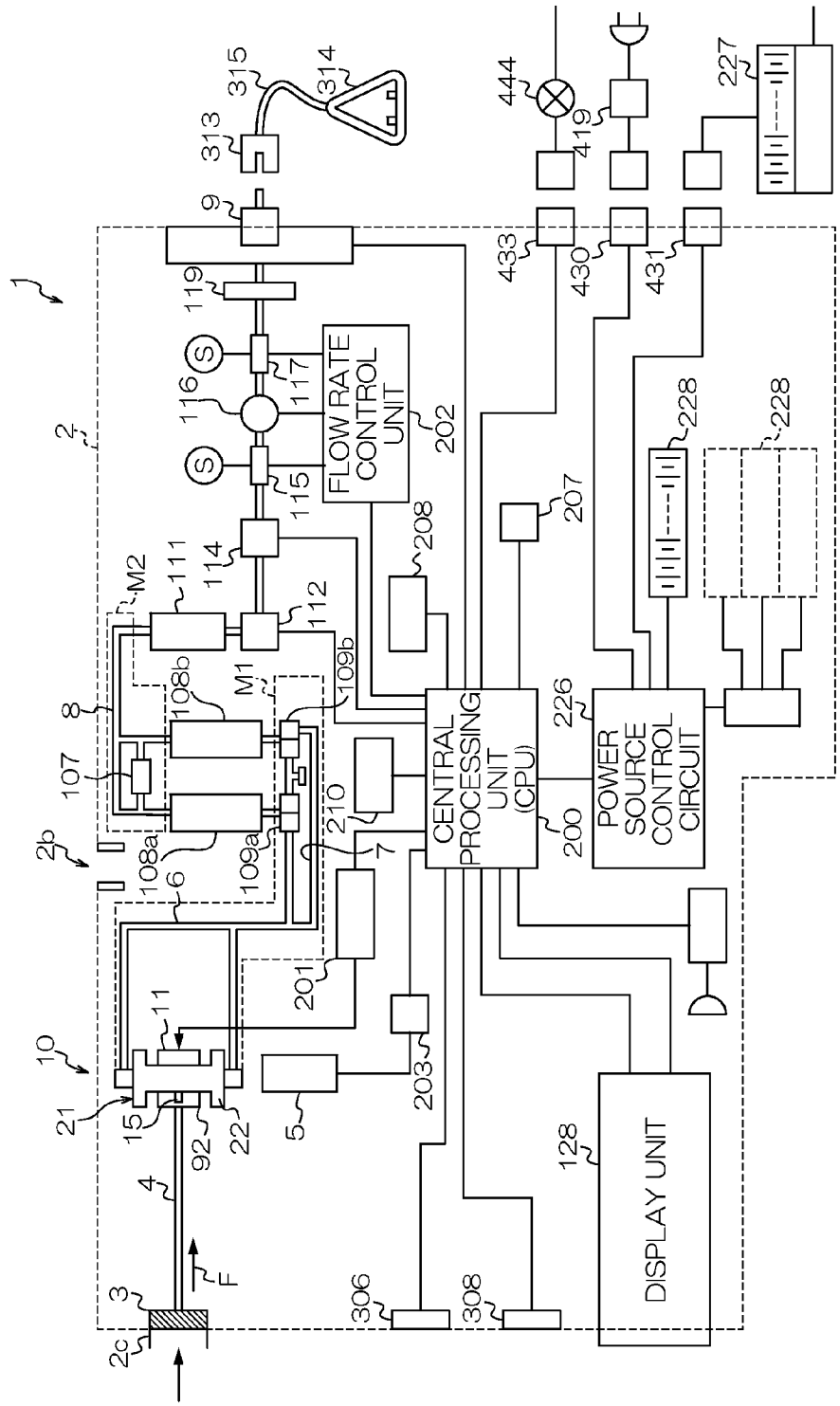
F I G. 1

F I G.3
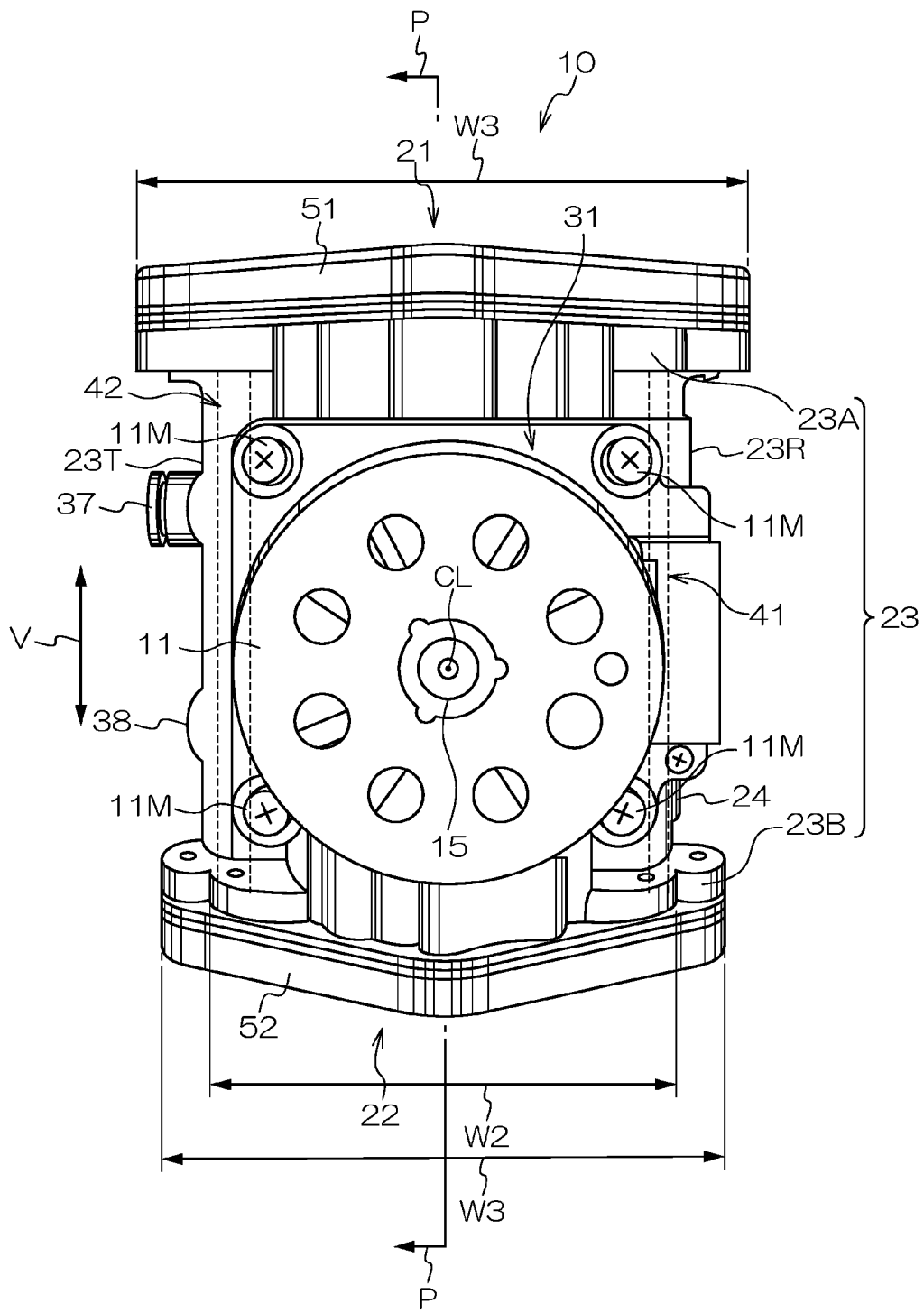

F I G.6
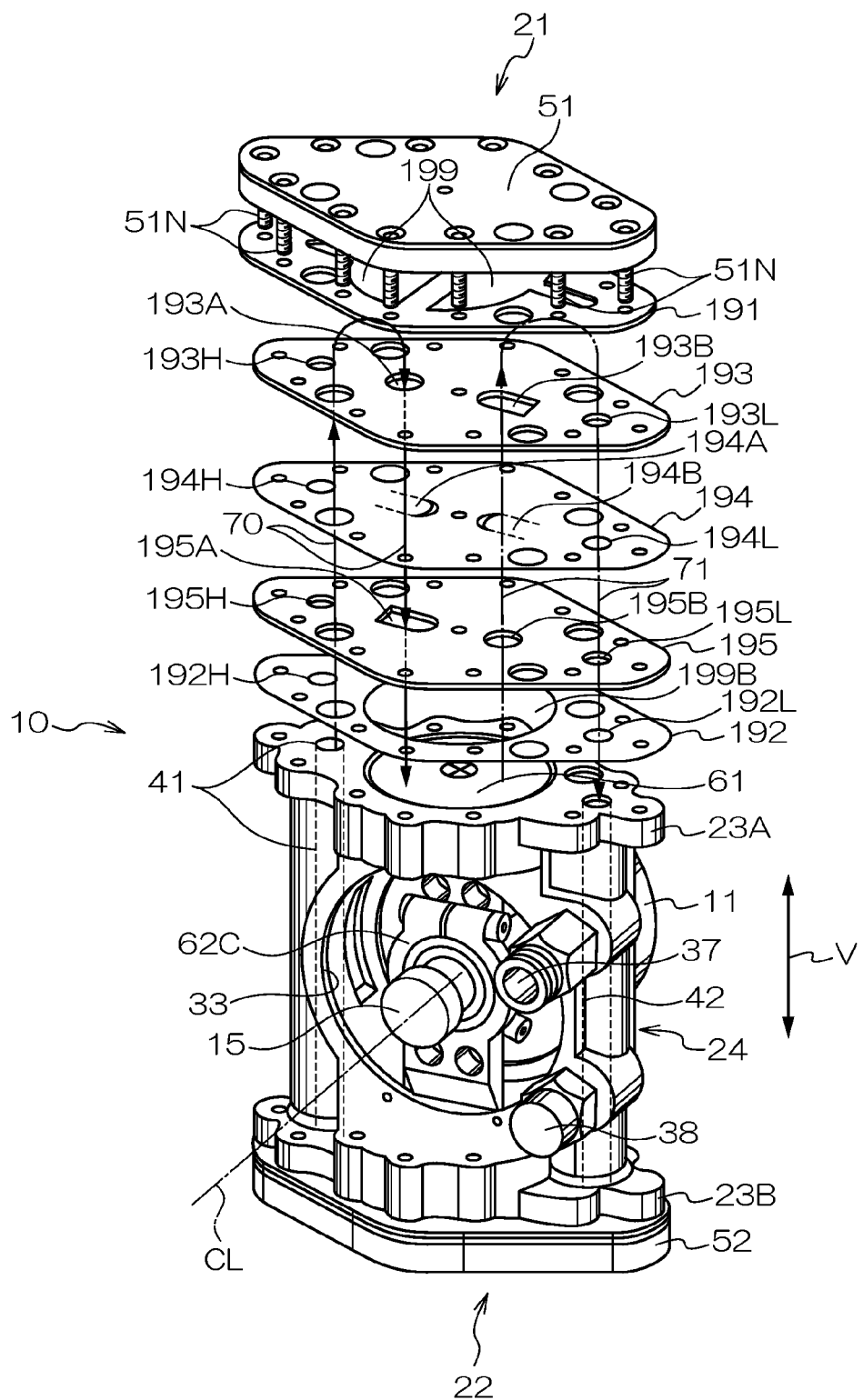

F I G. 8
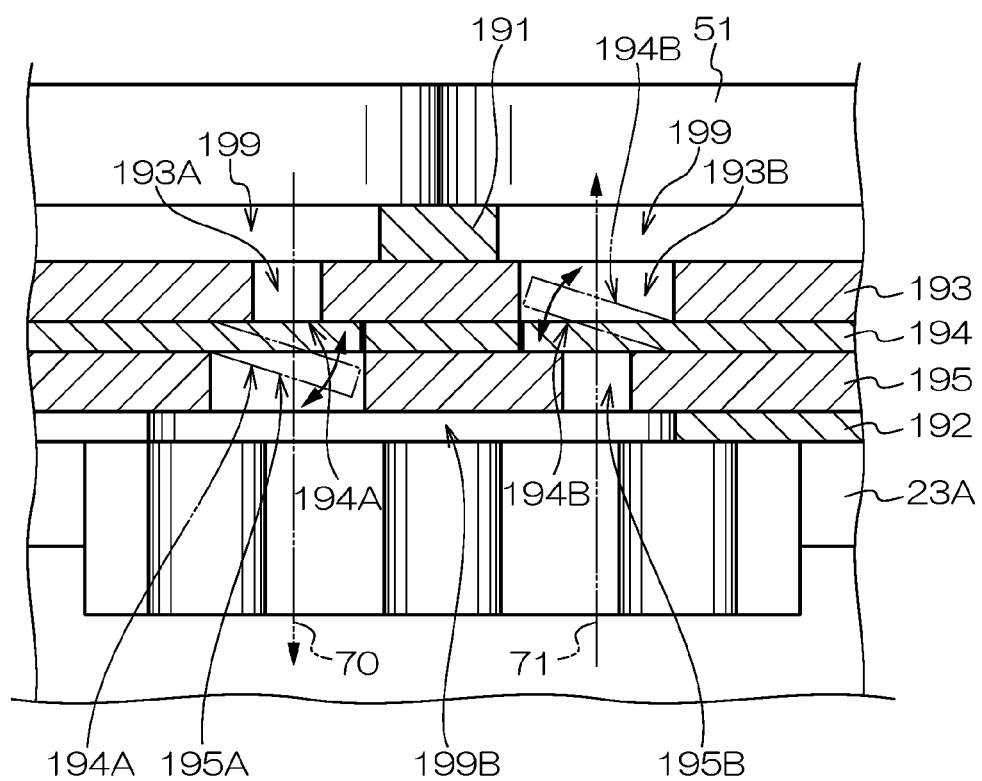

F I G. 10
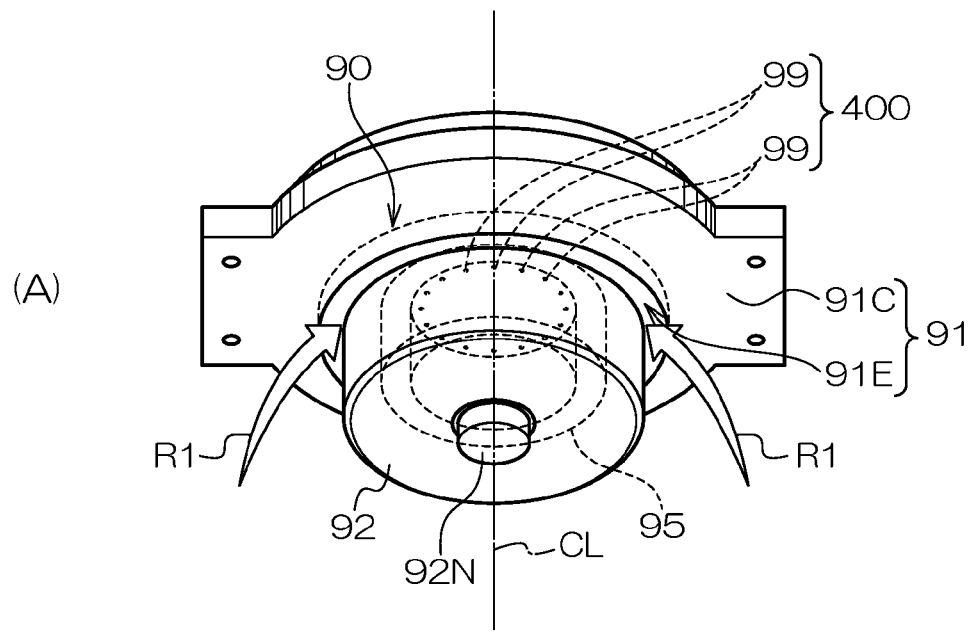
(A)
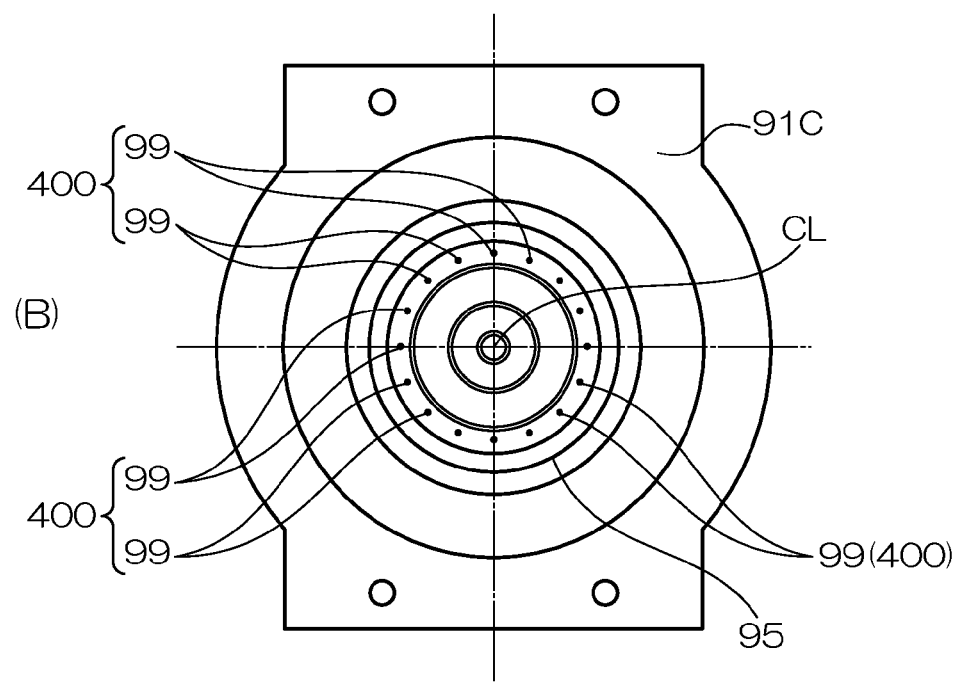
(B)

F I G.11
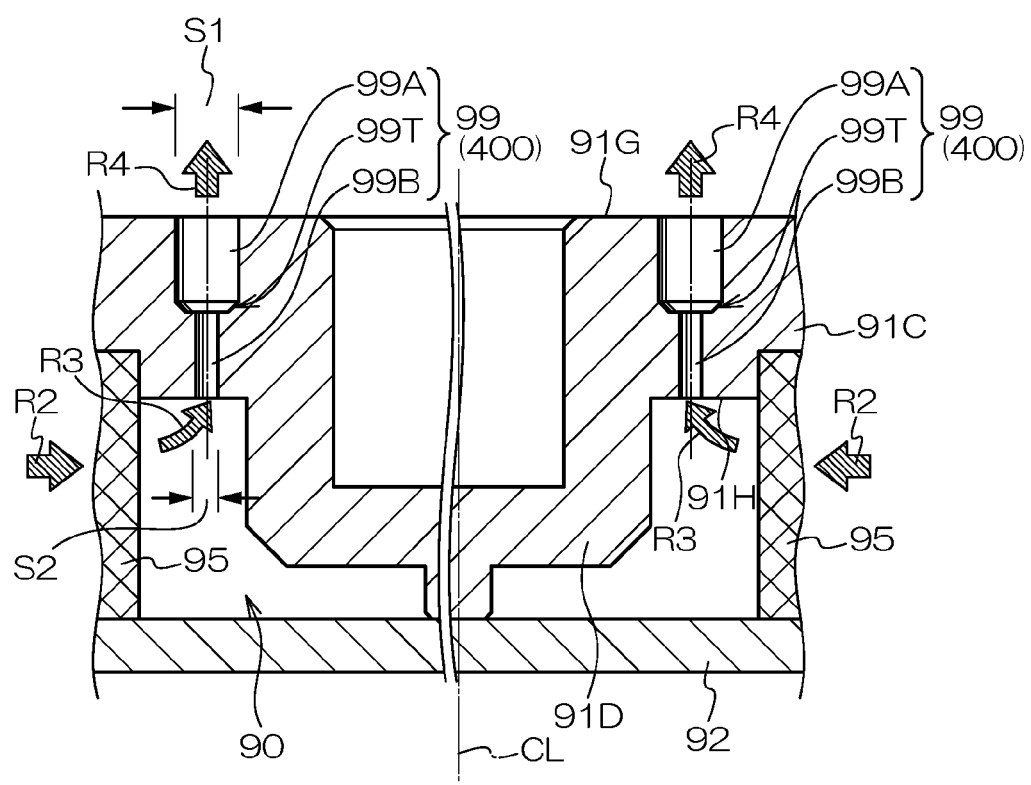

F I G. 12
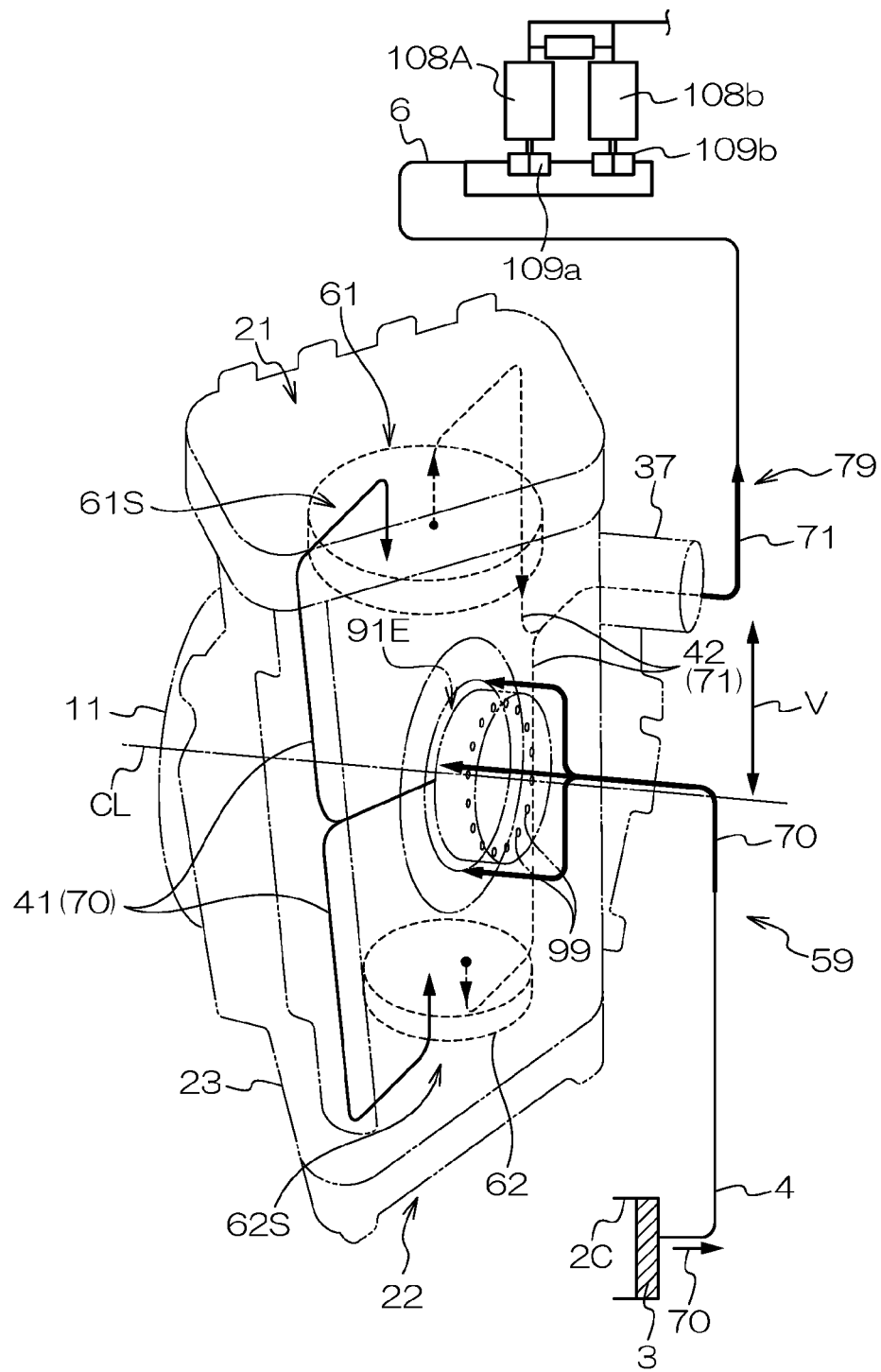

F I G.13
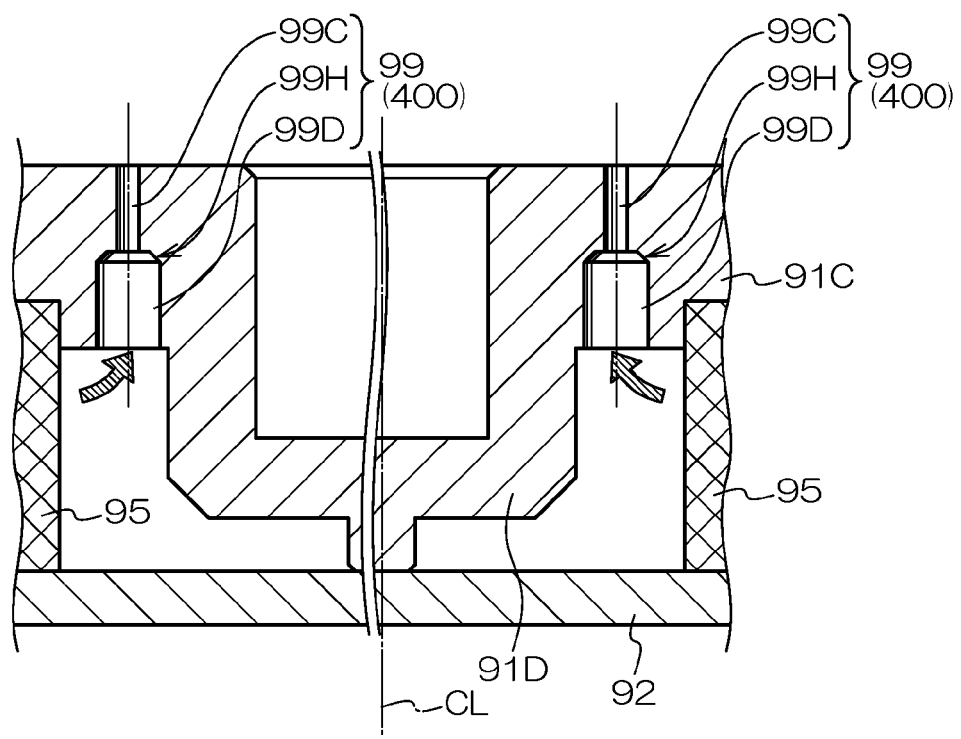

COMPRESSOR AND OXYGEN CONCENTRATOR

TECHNICAL FIELD

The present invention relates to a compressor and to an oxygen concentrator having the compressor. More particularly, the present invention relates to a compressor and an oxygen concentrator for medical uses capable of supplying oxygen by compressing intake raw air and feeding the compressed air to an adsorbent.

BACKGROUND ART

In oxygen concentrators, oxygen is obtained in accordance with a pressure swing adsorption method in which oxygen in raw air is caused to pass through, for instance, a zeolite or the like, as an adsorbent, that selectively adsorbs nitrogen.

An air intake opening for intake of raw air is provided in a main body cover of an oxygen concentrator of this type. Raw air taken in via this air intake opening is compressed by a compressor, as a compression unit, to generate compressed air thereby. The compressed air is fed to an adsorbent-packed adsorption barrel, where nitrogen is adsorbed onto the adsorbent, to yield oxygen as a result. The generated oxygen is stored in a tank and is brought to a state that enables supply of a predetermined flow rate of oxygen from the tank, via a reducing valve or a flow rate setting unit. Thereby, a patient can inhale the oxygen using an implement such as a nasal cannula.

For instance, patients having impaired lung function and being under home oxygen therapy can breathe oxygen safely even when in bed, and can sleep hence soundly, if such an oxygen concentrator is installed at a site where AC power source (commercial AC power source) can be used.

Preferably, the oxygen concentrator makes very little noise, in particular, when used in bed by patients under home oxygen therapy. Preferably, the noise of the oxygen concentrator does not exceed, for instance, the noise level of indoor air conditioning.

Oxygen concentrators used for long-term oxygen therapy, which is effective as a therapy for patients having a respiratory disease such as chronic bronchitis, are ordinarily not transportable, and are not configured to be carried to such sites as the patient may move to. When the patient is forced to go out, he/she must inhale concentrated oxygen out of an oxygen cylinder, being a container of a predetermined capacity filled with oxygen and placed on a cart that is pushed by the patient. Such oxygen and cylinders must be filled at dedicated facilities. Thus, transportable and/or mobile oxygen concentrators have been proposed wherein the transportable or mobile oxygen concentrator is provided with a battery-drivable compressor that comprises a compression unit for generating compressed air by taking raw air in, and with a pressure reduction unit for generating reduced-pressure air (Patent document 1).

Patent document 1: Japanese Patent Application Laid-open 2002-45424

DISCLOSURE OF THE INVENTION

In the compressor of the above-described conventional oxygen concentrator, a piston crankcase has one large air inlet for intake of raw air. A piston at a head section is operated through rotation of the motor output shaft of the compressor, and raw air in the form of external air is directly sucked through the one air inlet as a result into the piston, to generate compressed air thereby. Upon operation of the compressor, however, substantial air intake noise is generated during intake of the raw air that is taken via an air intake opening of the main body cover into the crankcase of the piston, through an air inlet. The compressor becomes a noise source of the oxygen concentrator on account of this air intake noise. The noise may leak out of the main body cover via a raw air intake port in the main body cover, or may get across to the exterior, in the form of transmitted noise, via the main body cover, or may trigger resonance in the main body cover. In particular, direct leaks of raw air intake noise to the exterior, in the form of noise that passes through the air intake port of the main body cover, must be prevented. It would thus be desirable to allow compressed air to be generated, reliably and with low noise, through suction of raw air towards the piston.

It is an object of the present invention to provide a compressor and an oxygen concentrator having reduced raw air intake noise that occurs upon intake of raw air and generation of compressed air.

The compressor of the present invention is a compressor that generates compressed air by compressing raw air, wherein the compressor has: a case section; a driving motor that is provided in the case section and that has an output shaft; a head section operated by rotation of the output shaft of the driving motor and that sucks and compresses the raw air to generate thereby the compressed air; and a raw air intake section formed of a plurality of raw air intake holes for taking the raw air into the case section and supplying the raw air to the head section.

By virtue of the above configuration, raw air intake noise as generated during intake of raw air and generation of compressed air can be reduced by causing the raw air to be distributedly taken in via the plurality of raw air intake holes.

Preferably, the raw air intake holes of the raw air intake section are arrayed around a rotation center axis of the output shaft at the center of the holes, and these raw air intake holes are covered by a cylindrical hood member.

By virtue of the above configuration, the raw air can be distributedly taken into the case section via the raw air intake holes. Also, the raw air intake holes are covered by the cylindrical hood member. This allows preventing the raw air intake holes from being exposed to the exterior, and allows reducing air intake noise.

Preferably, the driving motor is provided at a first side face section of the case section; and the raw air intake section of the output shaft is provided at a second side face section on an opposite side to the first side face section of the case section.

In the above configuration, the driving motor and the raw air intake section can be respectively disposed on the first side face section and on the opposite second side face section of the case section. This affords a smaller compressor.

Preferably, a filter that removes impurities from the raw air is provided halfway in a flow path of introducing the raw air that is introduced into the raw air intake section from the hood member, and the filter is covered by the hood member.

By virtue of the above configuration, raw air that is introduced into the raw air intake section via the opening must necessarily pass through the filter. This enables raw air intake in a state where impurities such as dust and dirt have been removed from the raw air, and allows the filter to be covered by the hood member.

Preferably, the head section of the compressor has a first head section provided on a first end section side of the case section and a second head section provided on a second end section side of the case section; the driving motor is accommodated in a region formed by an outline portion of the first head section and an outline portion of the second head section, in the first side face section of the case section; and the hood member and the raw air intake section are accommodated in a region formed by the outline portion of the first head section and the outline portion of the second head section, in the second side face section of the case section.

The above configuration allows achieving a smaller, lighter and thinner compressor.

An oxygen concentrator of the present invention is an oxygen concentrator provided with a compressor that generates compressed air by compressing raw air, and an adsorption member that holds an adsorbent that adsorbs nitrogen from the compressed air, wherein the compressor has: a case section; a driving motor that is provided in the case section and that has an output shaft; a head section operated by rotation of the output shaft of the driving motor and that sucks and compresses the raw air to generate thereby the compressed air; and a raw air intake section formed of a plurality of raw air intake holes for taking the raw air into the case section and supplying the raw air to the head section.

In the oxygen concentrator of the present invention, by virtue of the above configuration, raw air intake noise as generated during intake of raw air and generation of compressed air can be reduced by causing the raw air to be distributedly taken in via the plurality of raw air intake holes.

The present invention succeeds in providing a compressor that allows reducing raw air intake noise as generated during intake of raw air and generation of compressed air, such that the compressor exhibits a low noise level, even if no soundproofing member is provided within the main chassis. The invention allows providing also a small, lightweight oxygen concentrator that uses such a compressor.

BRIEF DESCRIPTION OF THE DRAWINGS

FIG. 1 is a block diagram illustrating a preferred embodiment of an oxygen concentrator provided with a compressor of the present invention;

FIG. 3 is a perspective-view diagram of the compressor illustrated in FIG. 2 viewed from direction U;

FIG. 6 is a perspective-view diagram of an exploded first head section of the compressor of FIG. 2;

FIG. 8 is a cross-sectional diagram illustrating the stack structure of the first head section in the compressor of FIG. 2;

FIG. 10(A) is a perspective-view diagram illustrating an output shaft holding member, and FIG. 10(B) is a front-view diagram illustrating the shape of a disc portion of the output shaft holding member;

FIG. 11 is a diagram illustrating the cross-sectional shape of an air intake hole;

FIG. 12 is a diagram illustrating an outline shape of a compressor, denoted by a two-dot chain line, and a raw air introduction channel and a discharge channel, denoted by arrows, in the compressor;

FIG. 13 is a cross-sectional diagram illustrating another embodiment of an air intake hole of the present invention;

EMBODIMENT FOR CARRYING OUT THE INVENTION

Preferred embodiments of the present invention are explained in detail below with reference to accompanying drawings.

Figure 2:
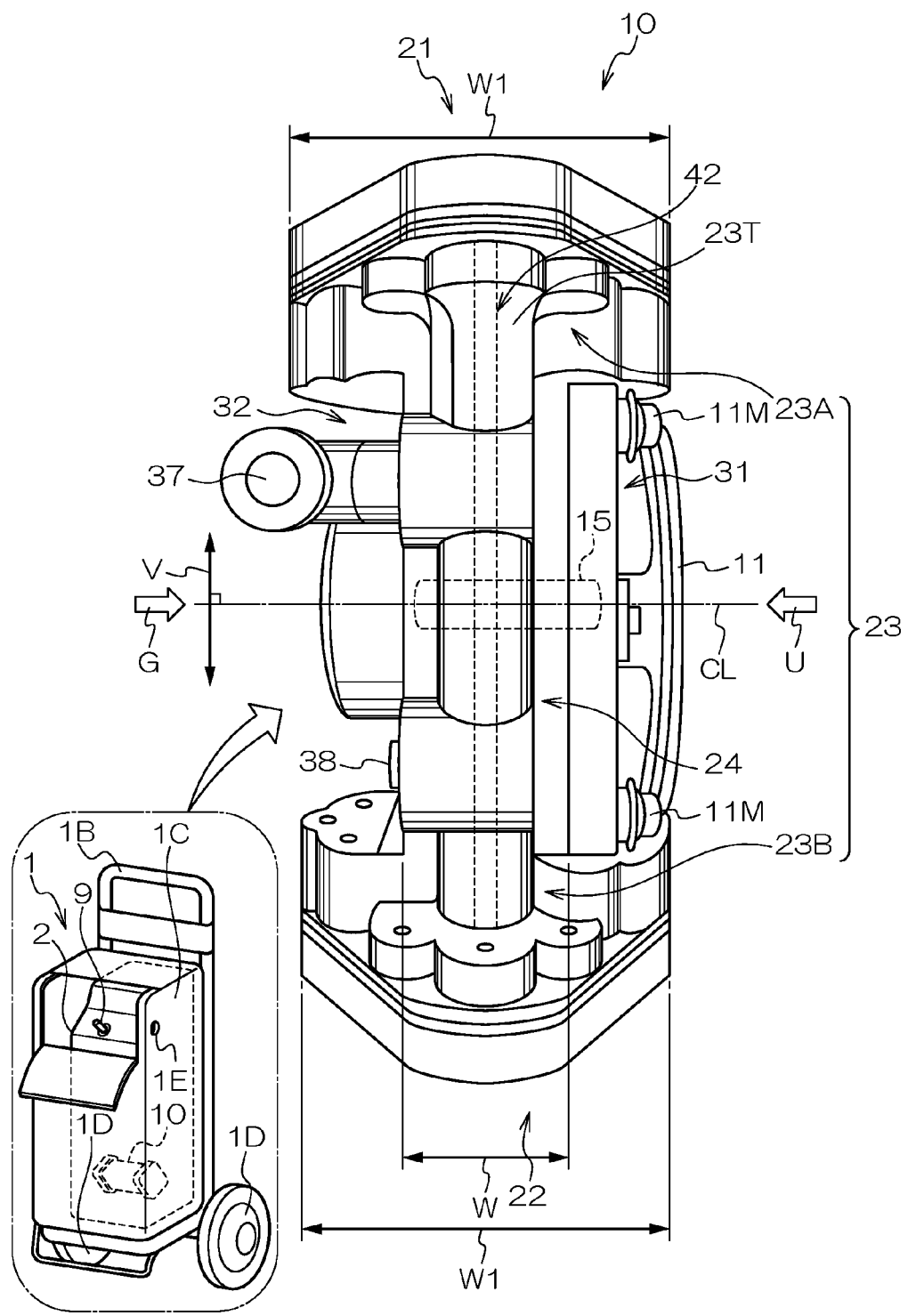
FIG. 2 is a perspective-view diagram illustrating an external-view example of the oxygen concentrator of FIG. 1 and illustrating the front face of a compressor.

The below-described modes for carrying out the invention are appropriate specific examples of the present invention, and may have various technically preferred limitations. Unless the present invention is particularly limited by the subject matter set forth in the explanation below, however, the scope of the present invention is not limited to any such modes. FIG. 1 is a block diagram illustrating a preferred embodiment of an oxygen concentrator provided with a compressor of the present invention. FIG. 2 is a perspective-view diagram illustrating an external-view example of the oxygen concentrator of FIG. 1 and illustrating the front face of the compressor.

In a preferred embodiment, an oxygen concentrator 1 illustrated in FIG. 1 is a portable (also referred to as transportable or mobile) oxygen concentrator, as schematically exemplified in FIG. 2. As illustrated in FIG. 2, a main chassis 2 of the oxygen concentrator 1 is accommodated in a holding case 1C as an accessory that in turn comprises accessories in the form of a handle 1B and wheels 1D. The length of the handle 1B can be adjusted in the vertical direction. The compressor 10 is disposed, for instance, at the bottom of the main chassis 2. A hole 1E for letting through a tube 315 of a nasal cannula 314 of FIG. 1 is provided in the holding case 1C.

The oxygen generation principle in the oxygen concentrator 1 illustrated in FIG. 1 and FIG. 2 is, for instance, a compressed-air pressure swing adsorption method (PSA: positive pressure swing adsorption) by compressed air. In a positive pressure swing adsorption method relying on compressed air alone, nitrogen is adsorbed through feeding of compressed air alone through the interior of an adsorption barrel. A positive pressure swing adsorption method is advantageous in that the compressor 10 is smaller and lighter than in a vacuum-pressure swing adsorption method (VPSA) that utilizes both compressed air and reduced-pressure air.

The double lines illustrated in FIG. 1 denote ducts that constitute flow passages of raw air, oxygen and nitrogen gas. The thin solid line denotes wiring for power source supply or for electric signals. The broken line denotes a main chassis 2 of the oxygen concentrator 1 illustrated in FIG. 1. The main chassis 2 is a hermetic container serving as the main body cover that seals the elements that are disposed within the main chassis 2. For instance, the main chassis 2 is an injection molding resin article formed out of a thermoplastic resin having impact resistance.

The main chassis 2 illustrated in FIG. 1 has an air intake port 2c for introduction of raw air, in the form of external air, and an outlet port 2b for discharge. A filter 3 for removing impurities such as dirt and dust in the air is disposed at the air intake port 2c. Upon operation of the compressor 10, raw air is introduced into the compressor 10 via the filter 3 of the air intake port 2c and via an inner duct 4, in direction F.

In FIG. 1, the raw air is introduced to the compressor 10 via the duct 4 and is compressed to yield compressed air. Heat is generated upon compression of the raw air. Accordingly, the compressed air discharged out of the compressor 10 is cooled through rotation of a blower fan 5. Cooling of the compressed air allows suppressing rises in the temperature of a zeolite, as an adsorbent, the performance whereof drops at high temperatures. Sufficient performance of the adsorbent for generating oxygen through adsorption of nitrogen can be ensured as a result, so that oxygen can be concentrated to about 90% or above.

A first adsorption barrel 108*a* and a second adsorption barrel 108*b* in FIG. 1, as an example of an adsorption member, are disposed in parallel in a vertical direction. Respective three-way switching valves 109*a*, 109*b*, as switching valves, are connected to the first adsorption barrel 108*a* and the second adsorption barrel 108*b*. One end section of the three-way switching valve 109*a* is connected to a duct 6, the three-way switching valve 109*a* and the three-way switching valve 109*b* are connected to each other, and further, one end section of the three-way switching valve 109*b* is connected to a duct 7. The duct 7 and the duct 6 are connected to each other. The duct 7 is connected to the duct 6 in order to perform a purification process of causing unwanted gas to desorb from the interior of the first adsorption barrel 108*a* and the second adsorption barrel 108*b*. The three-way switching valves 109*a* and 109*b* are respectively connected to the first adsorption barrel 108*a* and the second adsorption barrel 108*b*. The compressed air generated in the compressor 10 is alternately supplied to the first adsorption barrel 108*a* and the second adsorption barrel 108*b* via the duct 6 and the three-way switching valves 109*a*, 109*b*.

A zeolite, as a catalytic adsorbent, is stored in the first adsorption barrel 108*a* and the second adsorption barrel 108*b* in FIG. 1. The zeolite is, for instance, a zeolite X in which the $Si_2O_3/Al_2O_3$ ratio ranges from 2.0 to 3.0. The adsorption amount per unit weight is increased through the use of a zeolite in which at least 88% or more of $Al_2O_3$ tetrahedral units are bonded to lithium cations. In particular, the zeolite has preferably a granulometric value smaller than 1 mm, and at least 88% or more of tetrahedral units are fused with lithium cations. The amount of raw air that is used as required for oxygen generation can be reduced through the use of a zeolite, as compared with cases in which other adsorbents are used. As a result, the compressor 10 for generating compressed air can be made smaller and less noisy.

As illustrated in FIG. 1, a uniform pressure valve 107, comprising a check valve, a throttle valve and an on-off valve, is connected to the outlets of the first adsorption barrel 108*a* and the second adsorption barrel 108*b*. A merging duct 8 is connected to the downstream side of the uniform pressure valve 107. A product tank 111 is connected to the duct 8. The product tank 111 is a container for storing oxygen of a concentration of about 90% or higher that is separated at the first adsorption barrel 108*a* and the second adsorption barrel 108*b*.

As illustrated in FIG. 1, a pressure regulator 112 is connected to the downstream side of the product tank 111. The pressure regulator 112 is a regulator for automatically adjusting the pressure of oxygen at a predetermined level on the outlet side of the product tank 111. An oxygen concentration sensor 114 of zirconia type or ultrasonic type is connected to the downstream side of the pressure regulator 112. The oxygen concentration sensor 114 detects oxygen concentration intermittently (every 10 to 30 minutes) or continuously.

As illustrated in FIG. 1, a proportional-opening valve 115 is connected to the oxygen concentration sensor 114. On the basis of a signal from a flow rate control unit 202, prompted by a command by a central processing unit 200, the proportional-opening valve 115 opens and closes in response to a setting button operation of an oxygen flow rate setting button 308. An oxygen flow rate sensor 116 is connected to the proportional-opening valve 115. A demand valve 117 is connected to the oxygen flow rate sensor 116 via a reduced-pressure air circuit board for breath synchronization control. The demand valve 117 is connected to the oxygen outlet 9 of the oxygen concentrator 1 via a sterile filter 119.

An adapter 313 of a nasal cannula 314 is removably connected to the oxygen outlet 9. The adapter 313 is connected to the nasal cannula 314 via a tube 315. With the nasal cannula 314, the patient can inhale, for instance, oxygen concentrated to about 90% or above, at a maximum flow rate of 1 L/minute. Performing breath synchronization control through control of the demand valve 117 elicits conceivably the same effect as supplying, to the patient, substantially a maximum 3 L/minute of oxygen concentrated to 90% or above as a result of breath synchronization control, given that the IE ratio (ratio between inspiration time (seconds)/expiration time (seconds)) is ordinarily 1:2.

A power source system illustrated in FIG. 1 is explained next.

A connector 430 of an AC (commercial AC) power source illustrated in FIG. 1 is connected to an AC adapter 419 of switching regulator type. The AC adapter 419 rectifies AC voltage from a commercial AC power source to a predetermined DC voltage. A built-in battery 228 is provided, for instance, at the bottom of the main chassis 2. An external battery 227 is removably provided via a connector 431. A power source control circuit 226 is electrically connected to connectors 430, 431.

The built-in battery 228 and the external battery 227 are repeatedly rechargeable secondary batteries. The built-in battery 228 can be charged by receiving power supply from the power source control circuit 226. The external battery 227 can also be charged by receiving power supply from the power source control circuit 226. Ordinarily, however, the external battery 227 is repeatedly charged using a battery charger that is provided separately.

As a result, control of the power source control circuit 226 by the central processing unit 200 of FIG. 1 makes it possible to automatically switch to one supply state from among a total of three system power supply states, namely a first power supply state in which power supply is received from the AC adapter 419, a second power supply state in which power supply is received from the built-in battery 228, and a third power supply state in which power supply is received from the external battery 227. The built-in battery 228 and the external battery 227 may be lithium ion or lithium hydride ion secondary batteries that can be fully charged during recharge thanks to their small memory effect upon charging. The built-in battery 228 and the external battery 227 may also be conventional nickel cadmium batteries or nickel hydride batteries. For emergencies, the external battery 227 may be configured, for instance, in the form of a box of C-size batteries that are procurable anywhere.

The central processing unit 200 of FIG. 1 is electrically connected to a motor control unit 201 and a fan motor control unit 203. The central processing unit 200 stores a program that switches between optimal operation modes in accordance with the amount of oxygen to be generated. In response to commands from the central processing unit 200, the motor control unit 201 and the fan motor control unit 203 automatically drive the compressor 10 and the blower fan 5 at high speed, when a substantial amount of oxygen is to be generated, and cause the compressor 10 and the blower fan 5 to be rotationally driven at a lower speed when little oxygen is to be generated. The central processing unit 200 has built therein a ROM (read-only memory) that stores a predetermined operation program. An external storage device 210, a volatile memory 208, a temporary storage device and a circuit 207 comprising a real-time clock are also electrically connected to the central processing unit 200. The central processing unit 200 can access stored content through connection to a communication circuit 444 or the like via an external connector 433.

A control circuit (not shown) that performs control, as well as flow rate control unit 202 and the oxygen concentration sensor 114, are electrically connected to the central processing unit 200 in such a manner that unwanted gas in the first adsorption barrel 108a and the second adsorption barrel 108b is desorbed through on-off control of the three-way switching valves 109a, 109b and the uniform pressure valve 107 illustrated in FIG. 1. Also, a oxygen flow rate setting button 308, a display unit 128 and a power source switch 306 are electrically connected to the central processing unit 200 illustrated in FIG. 1.

The oxygen flow rate setting button 308, for instance, allows setting an oxygen flow rate, of oxygen concentrated to about 90% or above, each time the button is operated in 0.01 L (liter) stages from 0.25 L per minute to a maximum of 1 L per minute. Substantially 3 L/minute of oxygen at a concentration of 90% or higher is supplied to the patient through breath synchronization control. Accordingly, there is preferably provided a synchronization mode selection switch (not shown) that can be operated by the patient. The display unit 128 that is used may be for instance a display device such as a liquid crystal display. On the display unit 128 there can be displayed, for instance, display items such as an operation indicator, an oxygen indicator, a synchronization mode, a charge indicator, remaining battery power, cumulative time, oxygen flow rate and so forth. For instance, a display "synchronization mode" may be lighted up in green during the time at which breath synchronization control is active.

An explanation follows next, with reference to FIG. 2 to FIG. 7, on an example of a preferred structure of the compressor 10 illustrated in FIG. 1.

Figure 4:
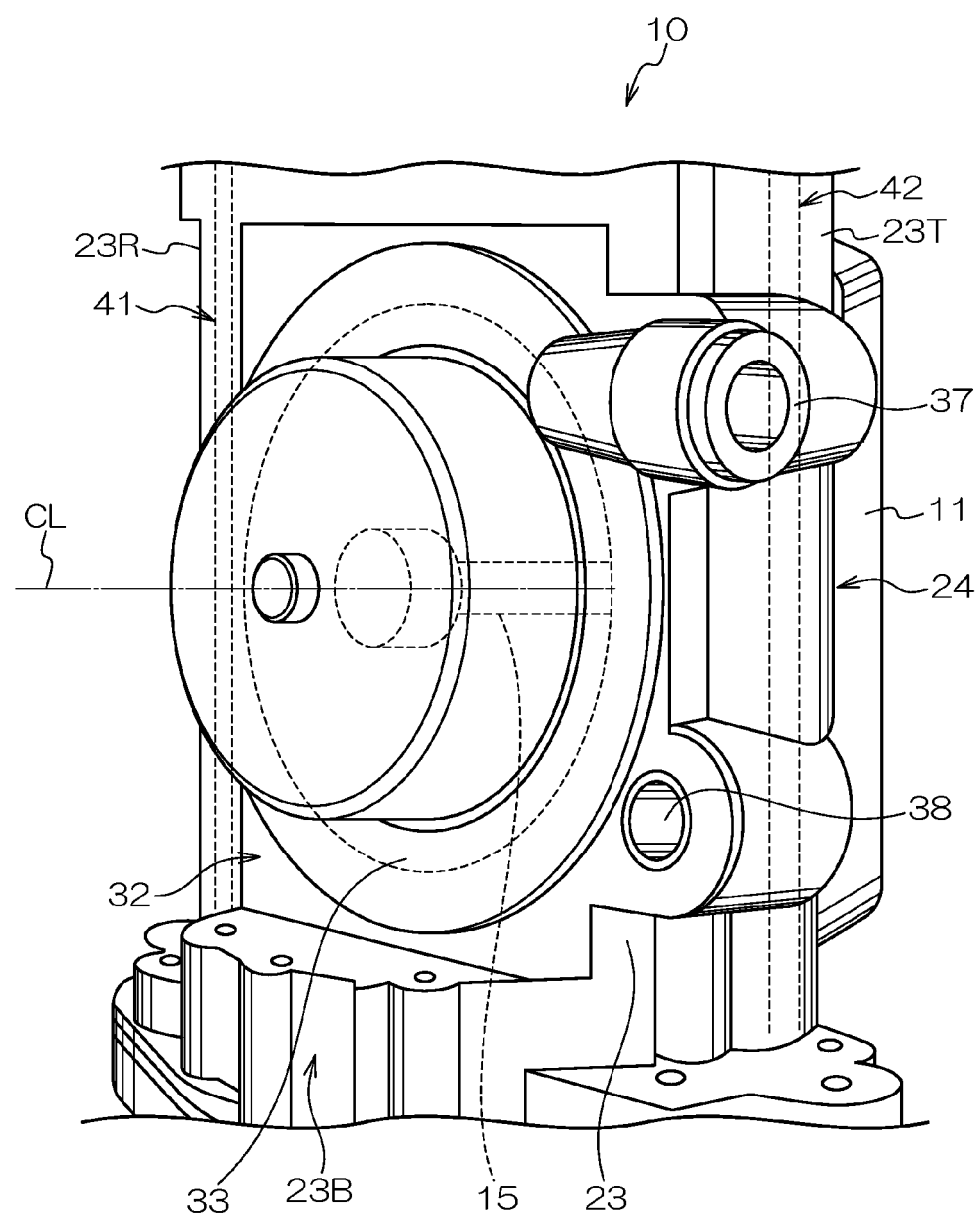
FIG. 4 is a perspective-view diagram of the compressor illustrated in FIG. 2 viewed from direction G.
Figure 5:
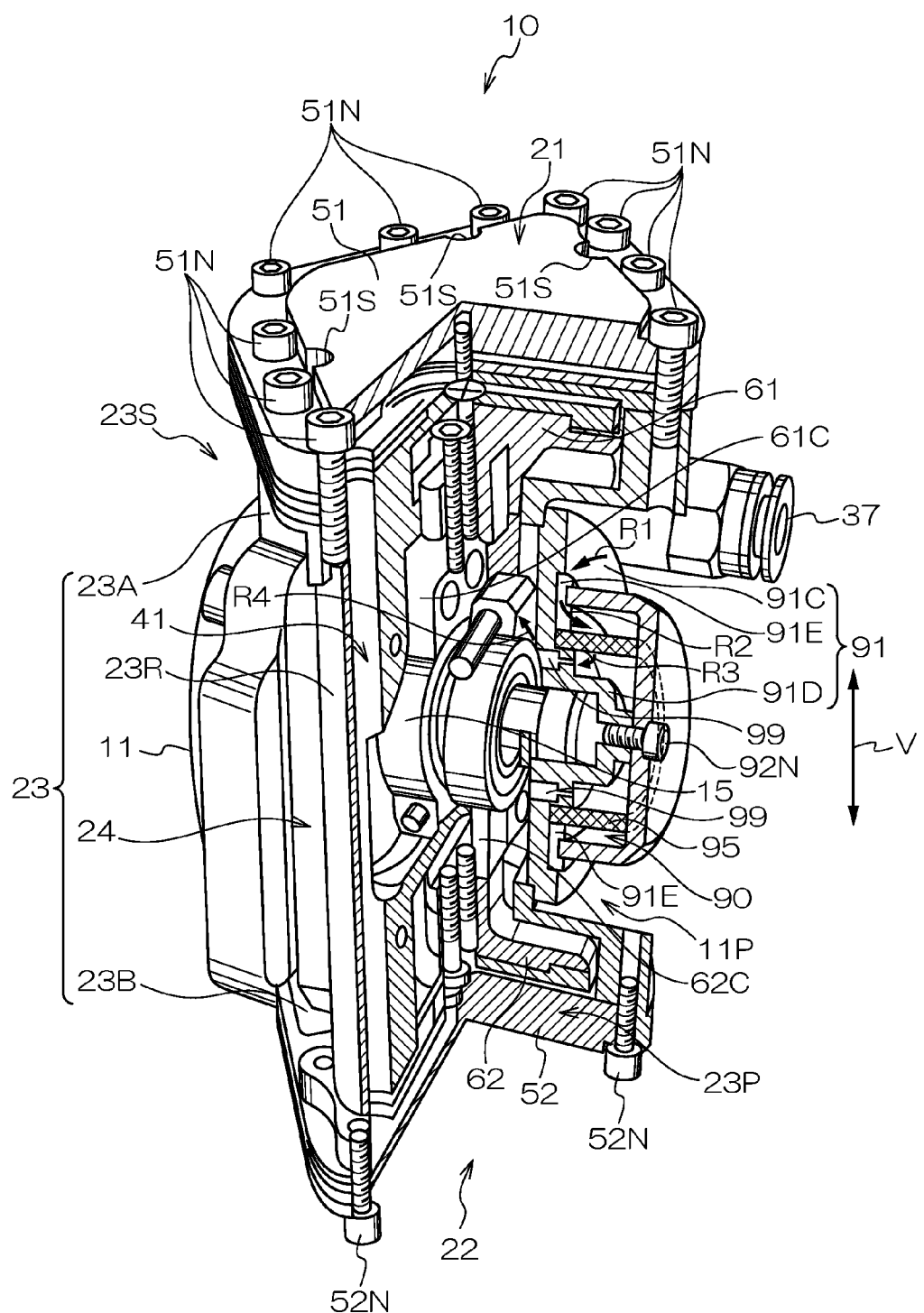
FIG. 5 is a perspective-view diagram illustrating an internal structure of the compressor of FIG. 2, having part thereof removed, as viewed in an oblique direction from the top.
Figure 7:
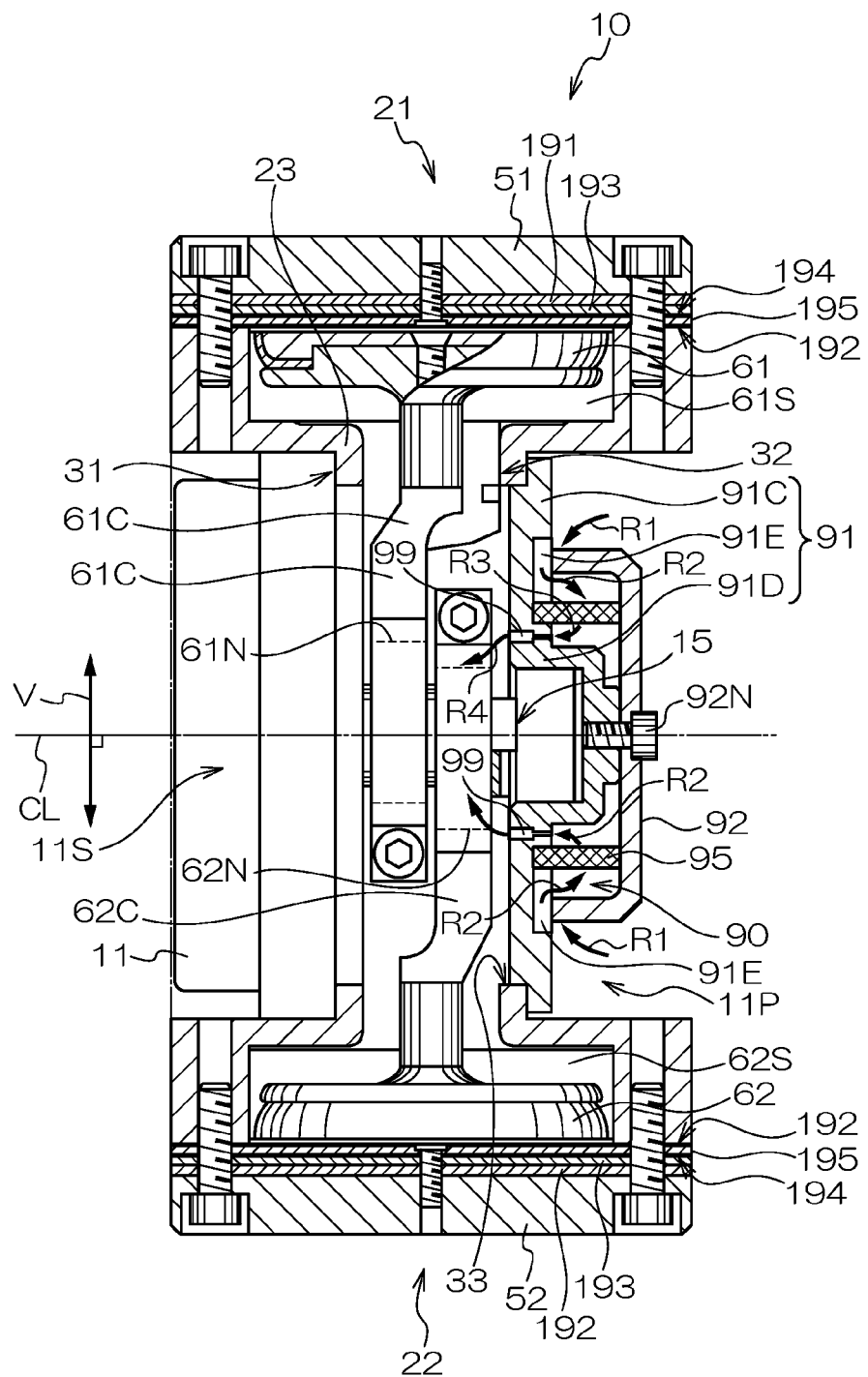
FIG. 7 is a cross-sectional diagram illustrating the compressor of FIG. 3, along line P-P in direction V.

FIG. 2 is a perspective-view diagram of the compressor 10 viewed from the front. FIG. 3 is a perspective-view diagram of the compressor 10 illustrated in FIG. 2 viewed from direction U. FIG. 4 is a perspective-view diagram of the compressor 10 illustrated in FIG. 2 viewed from direction G. FIG. 5 is a perspective-view diagram illustrating an internal structure of the compressor 10 of FIG. 2, having part thereof removed, as viewed in an oblique direction from the top. FIG. 6 is a perspective-view diagram illustrating an exploded first head section of the compressor 10 of FIG. 2. FIG. 7 is a cross-sectional diagram illustrating the compressor of FIG. 3, along line P-P in direction V.

The compressor 10 illustrated in FIG. 2 and FIG. 3 is used to cause compressed air to be fed to the interior of the first adsorption barrel 108a and the second adsorption barrel 108b illustrated in FIG. 1, according to a positive pressure swing adsorption method (PSA) in which, as described above, only compressed air is generated, and nitrogen in the compressed air is adsorbed by the adsorbent in the first adsorption barrel 108a and the second adsorption barrel 108b.

The compressor 10 in FIG. 2 and FIG. 3 is a two-head compressor having a driving motor 11, a first head section 21, a second head section 22 and a case section 23, and is small and lightweight, having a total weight of about 300 g to 900 g in accordance with a configuration to be described later. The driving motor 11 is, for instance, a 1 L-class electric motor, but may be, for instance, a single-phase AC induction motor, or a single-phase 4-pole AC synchronous motor.

The first head section 21, the second head section 22 and the case section 23 illustrated in FIG. 2 are for instance made up of aluminum, which is a lightweight metal material, in order to achieve a lighter compressor. However, the foregoing sections can be made up of non-metal material, which is engineering plastic.

The first head section 21 illustrated in FIG. 2 is provided at a first end section (top end section) 23A of the case section 23. The second head section 22 is provided at a second end section (bottom end section) 23B of the case section 23. The first head section 21 and the second head section 22 are reciprocating-driving pump heads that are driven by one output shaft 15 of the driving motor 11. The first head section 21 and the second head section 22 are formed to a substantially vertical symmetrical shape with respect to a rotation center axis CL of the output shaft 15.

The revolutions of the output shaft 15 can be kept constant even upon fluctuation of power source voltage, and a piston of the first head section 21 and a piston of the second head section 22 can be reciprocally driven in direction V in a stable manner, if, for instance a synchronous motor is used as the driving motor 11 illustrated in FIG. 2. The driving motor 11, which is a synchronous motor, can rotate at synchronous revolutions, and hence power consumption can be reduced vis-á-vis that of an induction motor.

The first head section 21 and the second head section 22 illustrated in FIG. 1 allow stably supplying compressed air to the first adsorption barrel 108a and the second adsorption barrel 108b. The first adsorption barrel 108a and the second adsorption barrel 108b allow stably supplying oxygen, concentrated to 90% or above, at the set oxygen flow rate.

The structure of the case section 23 of the compressor 10 will be explained first with reference to FIG. 2 to FIG. 5.

As illustrated in FIG. 2 and FIG. 3, the case section 23, also called a crankcase, is disposed along direction V. Direction V is perpendicular to the rotation center axis CL. As illustrated in FIG. 2 and FIG. 3, the case section 23 has a main body 24, a first end section 23A and the second end section 23B. The first end section 23A is a portion at which the first head section 21 is attached, and the second end section 23B is a portion at which the second head section 22 is attached.

As illustrated in FIG. 2, the thickness W of the case section 23 is set to be fairly smaller than the width W1 of the first end section 23A and the second end section 23B. As illustrated in FIG. 3, another transversal width W2 of the case section 23 is set to be slightly smaller than another transversal width W3 of the first end section 23A and the second end section 23B. The width W of the case section 23 illustrated in FIG. 2 is set to be fairly smaller than the other transversal width W2 of the case section 23 illustrated in FIG. 3. As a result, the case section 23 can be made smaller and thinner than the first head section 21 and the second head section 22.

As illustrated in FIG. 2 and FIG. 3, a driving motor 11 is replaceably fixed, by way of a plurality of bolts 11M, to the first side section 31 of the case section 23. As illustrated in FIG. 4, a circular opening 33 is formed at the second side section 32 of the case section 23. The output shaft 15 of the driving motor 11 is disposed along the center of the opening 33, i.e. along the rotation center axis CL.

As indicated by the broken lines in FIG. 3 and FIG. 4, the case section 23 has a first communicating passage 41 and a second communicating passage 42. The first communicating passage 41 and the second communicating passage 42 are formed parallelly to direction V. The first communicating passage 41 is formed at a first side section 23R of the case section 23. The first communicating passage 41 is provided for the purpose of supplying raw air to the first head section 21 and the second head section 22.

The second communicating passage 42 illustrated in FIG. 3 and FIG. 4 is formed at a second side section 23T of the case section 23. The second communicating passage 42 is provided for the purpose of discharging such compressed air as results from compression of raw air at the first head section 21 and the second head section 22, out of the case section 23 via a compressed air discharge port 37. Another opening 38 is closed off by a cap 38P, as illustrated in FIG. 5.

FIG. 5 is explained next. FIG. 5 illustrates the internal structure of part of the compressor 10.

The first head section 21 has a head cover 51 and a first piston 61 at the top. The head cover 51 is fixed by a plurality of screws 51N, with equal force, against the first end section 23A of the case section 23. A connecting rod 61C is attached to the first piston 61. The connecting rod 61C is attached to the output shaft 15 by way of a bearing member.

As illustrated in FIG. 5, the head cover 51 and so forth is fixed by the plurality of screws 51N in such a manner that an equal fastening force is applied to the first end section 23A. This allows preventing leaks of air out of the first head section 21. Moreover, a plurality of recesses 51S for heat dissipation is formed in the head cover 51, as illustrated in FIG. 5. This allows enhancing the effect of heat dissipation during generation of compressed air. That is, heat is generated upon generation of compressed air through compression of raw air when the first piston 61 in the first head section 21 moves linearly along direction V, from the bottom dead center to the top dead center. This generated heat can be dissipated to the exterior, with good efficiency, by providing the recesses 51S for heat dissipation, whereby the heat-dissipation surface area is increased.

Similarly, the second head section 22 illustrated in FIG. 5 has a head cover 52 and a second piston 62 at the bottom. The bottom head cover 52 has the same shape as that of the top head cover 52. The bottom head cover 52 is fixed by a plurality of screws 52N, with equal force, against the second end section 23B of the case section 23. A connecting rod 62C is attached to the second piston 62. The connecting rod 62C is attached to the output shaft 15 by way of a bearing member. In the example of the figures the head cover 51 of the first head section 21 and the head cover 52 of the second head section 22 have a diamond shape.

As illustrated in FIG. 5, the head cover 52 and so forth is fixed by the plurality of screws 52N in such a manner that an equal fastening force is applied to the second end section 23B. This allows preventing leaks of air out of the second head section 22. A plurality of recesses (not shown) for heat dissipation are formed at the head cover 52 as well. This allows enhancing the effect of heat dissipation during generation of compressed air. That is, heat is generated upon generation of compressed air through compression of raw air when the second piston 62 in the second head section 22 moves linearly along direction V, from the bottom dead center to the top dead center. This generated heat can be dissipated to the exterior, with good efficiency, by providing the recesses for heat dissipation, whereby the heat-dissipation surface area is increased.

A structure example of the first head section 21 is explained next with reference to FIG. 6 and FIG. 7.

FIG. 6 is an exploded perspective-view diagram illustrating a first head section 21. FIG. 7 is a cross-sectional diagram illustrating the compressor of FIG. 3, along line P-P in direction V. The first head section 21 and the second head section 22 have the same stack structure, but with a reversed up-and-down relationship with respect to each other. Therefore, the structure of the first head section 21 will be explained as a representative instance.

FIG. 6 illustrates a head cover 51 of the first head section 21, upper and lower gaskets 191, 192, an upper member 193, a reed valve member 194 and a lower member 195. These members make up a head assembly. The head cover 51 can be evenly fixed to the first end section 23A of the case section 23, yet more reliably, by way of the plurality of bolts 51N, in a state where the gaskets 191, 192, the upper member 193, the reed valve member 194 as a valve member and the lower member 195 are sandwiched in the sequence illustrated in the figure. The gaskets 191, 192 are provided for the purpose of preventing leaks of raw air to the exterior during compression. The gasket 191 has an opening 199 and the gasket 192 has a circular opening 199B. The upper member 193 has openings 193A, 193B, and the lower member 195 has openings 195A, 195B.

The reed valve member 194 illustrated in FIG. 6 has two opposing reed valves 194A, 194B. The reed valve member 194 is an example of a valve member. The reed valve 194A is an example of a first valve, and the reed valve 194B is an example of a second valve.

The material of the reed valve member 194 is not a heavy and rigid metal sheet as in spring steel sheets conventionally used, but a thermoplastic resin material such as a polyester film, i.e. a material lighter than metals and that is tough, exhibits heat resistance up to 120° C., and has excellent gas barrier properties. The material of the reed valve member 194 has a thickness ranging from 0.08 to 0.12 mm, being preferably 0.1 mm, and has a weight ranging from 0.3 to 0.5 g, being preferably 0.45 g. Examples of polyester film that can be used include, for instance, a polyester film (trade name Lumirror) by TORAY INDUSTRIES, INC. A material having a thickness of 0.08 to 0.12 mm results in excellent sealability in terms of fitting to a hole thanks to appropriate deflection. Fitting to a hole becomes difficult on account of poorer deflection if the thickness exceeds 0.12 mm, while sealing performance is impaired on account of ready deflection if the thickness is smaller than 0.08 mm. Examples of the thermoplastic resin material of the reed valve member 194 that can be used, other than the abovementioned polyester, include, for instance, polyester resins such as polyethylene terephthalate, polyethylene naphthalate, polybutylene terephthalate or the like; and engineering plastics such as polyphenylene sulfide, polyether ether ketone, polyether sulfones, polyamides, polyimides and the like.

As illustrated in FIG. 6, raw air 70 denoted by a solid line arrow passes through the first communicating passage 41, through a hole 192H of the gasket 192, a hole 195H of the lower member 195, a hole 194H of the reed valve member 194, a hole 193H of the upper member 193, and an opening 199 of the gasket 191. Further, the raw air 70 passes through an opening 193A of the upper member 193, the reed valve 194A of the reed valve member 194, the opening 195A of the lower member 195 and the opening 199B of the gasket 192, to be supplied into the first piston 61.

In a case where the raw air 70 is thus supplied to the first piston 61 by way of the opening 193A of the upper member 193, the reed valve 194A of the reed valve member 194, the opening 195A of the lower member 195 and the opening 199B of the gasket 192, then the reed valve 194A of the reed valve member 194 deforms elastically downwards, from the solid line up to the broken line illustrated in FIG. 8. An opening and closing operation is performed as a result between the opening 193A of the upper member 193 and the opening 195A of the lower member 195. The reed valve 194A in the state indicated by the solid line closes the opening 193A, while the reed valve 194A in the state indicated by the broken line opens the opening 193A.

As shown in FIG. 6, the raw air 70 becomes compressed through displacement of the first piston 61 from the bottom dead center to the top dead center, whereupon compressed air 71 is generated. The compressed air 71 denoted by the broken line arrow passes through the opening 199B of the gasket 192, the opening 195B of the lower member 195, the reed valve 194B of the reed valve member 194, the opening 193B of the upper member 193 and the opening 199 of the gasket 191, and passes further through a hole 193 L of the upper member 193, a hole 194 L of the reed valve member 194, a hole 195 L of the lower member 195, and hole 192 L of the gasket 192, and via the second communicating passage 42, so that the compressed air 71 can be discharged out of the case section 23 via the discharge port 37.

In a case where the compressed air 71 is thus discharged by way of the opening 199B of the gasket 192, the opening 195B of the lower member 195, the reed valve 194B of the reed valve member 194 and the opening 193B of the upper member 193, then the reed valve 194B of the reed valve member 194 deforms elastically upwards, from the solid line up to the broken line illustrated in FIG. 8. An opening and closing operation is performed as a result between the opening 195B of the lower member 195 and the opening 193B of the upper member 193. The reed valve 193B in the state indicated by the solid line closes the opening 195B, while the reed valve 194A in the state indicated by the broken line opens the opening 195B.

Figure 9:
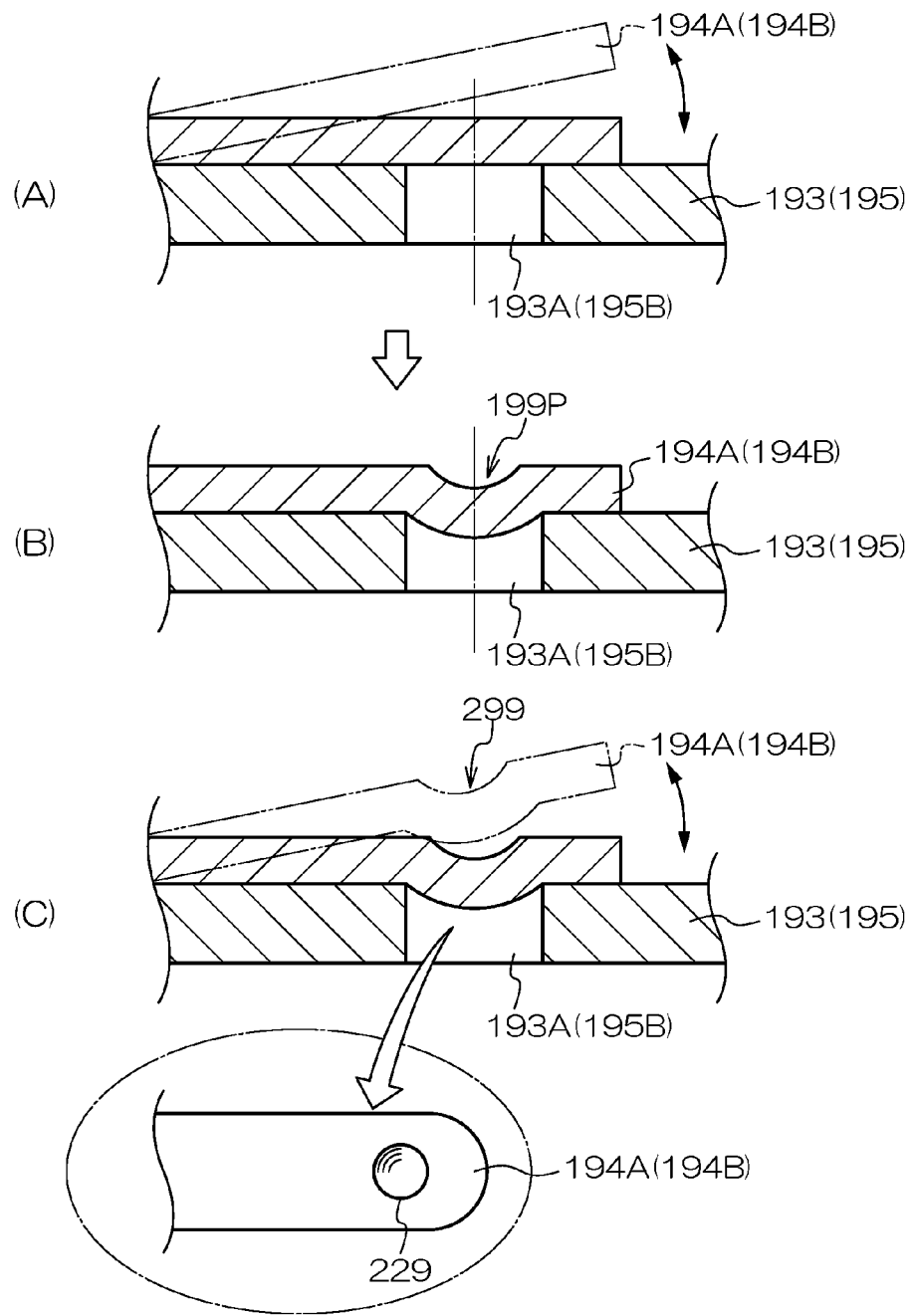
FIG. 9 is a diagram illustrating an operation example of two reed valves in a reed valve member of a compressor.

FIG. 9 illustrates the state of the reed valve 194A and the reed valve 194B of the reed valve member 194 when the latter open and close the opening 193A of the upper member 193 and the opening 195B of the lower member 195, respectively. The shape of the reed valve 194A and of the reed valve 194B are initially flat, as illustrated in FIG. 9(A), upon repeated opening and closing of the opening 193A of the upper member 193 and of the opening 195B of the lower member 195 by the reed valve 194A and the reed valve 194B, respectively. However, as illustrated in FIG. 9(B), a substantially semi-spherical recess 199P is formed in the reed valve 194A and the reed valve 194B as a result of fitting, through deflection on account of the resin characteristics, to the shape of the opening 193A, having circular cross-section, of the counterpart upper member 193, and the shape of the opening 195B, having a circular cross-section, of the lower member 195. As a result, the reed valve 194A and the reed valve 194B, as the first valve and the second valve can be closely fitted to the respective corresponding opening 193A and opening 195B. Gas blocking properties are accordingly enhanced.

In another embodiment of the present invention, illustrated in FIG. 9(C), a substantially semi-spherical recess 299 may be formed beforehand in the reed valve 194A, as the first valve, such that the recess 299 conforms to the shape of the opening 193A, having a circular cross-section, that corresponds to the reed valve 194A and through which raw air passes. A substantially semi-spherical recess 299 may be formed beforehand in the reed valve 194B, as the second valve, such that the recess 299 conforms to the shape of the opening 195B, having a circular cross-section, that corresponds to the reed valve 194B and through which raw air passes. Thus, the respective recesses 299 are formed beforehand, and hence the reed valve 194A and the reed valve 194B can be closely fitted to the respective corresponding openings 193A, 195B. Gas blocking properties are accordingly enhanced.

The reed valve 194A and the reed valve 194B of the reed valve member 194 are produced out of a plastic material which is a material that is lighter than metals and that boasts excellent toughness, heat resistance and gas blocking properties. This allows reducing significantly valve weight, generation of high-frequency metallic noise, and, as shown in FIG. 8, sealability of the opening 193A of the counterpart upper member 193 and the opening 195B of the counterpart lower member 195. Valve weight can be significantly reduced by using the reed valve 194A and the reed valve 194B of the plastic-made reed valve member 194, and the pressure upon initial opening of the valve can be also reduced. A reduction in cracking pressure, an increase in the flow rate of raw air and compressed air, as well as a reduction in the power source consumption by the motor are likewise afforded. Using the reed valve 194A and the reed valve 194B of the plastic-made reed valve member 194 allows reducing high-frequency metallic sounds, and allows realizing a soft sound quality having reduced whistling and free of shrill metallic sounds.

For instance, a 6 dB reduction (i.e. a reduction of ½ in terms of noise energy) of the noise upon intake of raw air and upon generation and discharge of compressed air was achieved herein by using a plastic-made reed valve member, as compared with using a conventional metallic reed valve member.

The pathways of the raw air 70 and the compressed air 71 in the first head section 21 are the same as in the second head section 22. The materials, shapes and operation of the reed valve 194A and the reed valve 194B of the reed valve member 194 in the first head section 21 are identical to those in the second head section 22.

Next, explanation is provided herewith reference to FIG. 7. FIG. 7 is a cross-sectional diagram illustrating the cross-sectional structure of the compressor 10 illustrated in FIG. 3, along line P-P in direction V. However, FIG. 7 depicts not the cross section of the driving motor 11 but the outer shape thereof.

In FIG. 7, the first head section 21 and the second head section 22 have a substantially vertical symmetrical structure with respect to the rotation center axis CL. The first piston 61 of the first head section 21 and the second piston 62 of the second head section 22 are horizontally-opposed pistons that reciprocate in opposite directions along direction V.

In the example of FIG. 7, the second head section 22 performs a suction process whereby raw air is sucked into the second cylinder 62S at the same time that the first head section 21 performs a suction process whereby raw air is sucked into the first cylinder 61S. The second head section 22 performs a compression process of generating compressed air in the second cylinder 62S, through compression of the sucked air, at the same time that the first head section 21 performs a compression process of generating compressed air in the first cylinder 61S through compression of the sucked air. That is, the second piston 62 is positioned at the bottom dead center in the second cylinder 62S at the time when the first piston 61 is positioned at the bottom dead center in the first cylinder 61S. The second piston 62 is positioned at the top dead center in the second cylinder 62S at the time when the first piston 61 is positioned at the top dead center in the first cylinder 61S.

Therefore, the first piston 61 and the second piston 62 reciprocate synchronically over an identical stroke length of about 1 mm to 10 mm, in mutually opposite directions. The amount of compressed raw air is small if the stroke length is shorter than 1 mm, while a stroke length longer than 10 mm results in a longer compressor 10. Thus, the raw air in the cylinders 61S, 62S is compressed when the first piston 61 and the second piston 62 are positioned at the top dead center, as in the example illustrated in FIG. 7. Conversely, the raw air is in a suctioned state within the cylinders 61S, 62S when the first piston 61 and the second piston 62 are positioned at the bottom dead center. The inner diameter of the cylinder 61S and the inner diameter of the cylinder 62S are identical, ranging from about 20 mm to 60 mm. The amount of compressed raw air is small if the inner diameter of the cylinder 61S and the inner diameter of the cylinder 62S are smaller than 20 mm. An inner diameter of the cylinder 61S and an inner diameter of the cylinder 62S greater than 20 mm makes it difficult to achieve a small and lightweight compressor 10.

An explanation follows next, with reference to FIG. 7, FIG. 5 and FIG. 3, on the structure of the driving motor 11, and on the output shaft 15 of the driving motor 11.

As illustrated in FIG. 3, the driving motor 11 is fixed to the case section 23, on the side of the first side face section 31, by way of bolts 11M. As illustrated in FIG. 7, the driving motor 11 is a substantially cylindrical motor formed to a thin profile along the rotation center axis CL. Preferably, the driving motor 11 is housed within a space 11S between the first head section 21 and the second head section 22. That is, the driving motor 11 is disposed to be accommodated within the space 11S in such a manner that the driving motor 11 does not protrude beyond the first head section 21 and the second head section 22 in the direction of the rotation center axis CL. In other words, the driving motor 11 is preferably accommodated within a region formed by the outline portion of the first head section 21 and by the outline portion of the second head section 22, at the first side face section 31 of the case section 23. As a result, the driving motor 11 is accommodated in such a way so as not to protrude beyond the outline portion of the compressor 10. This contributes to achieving a smaller, lighter and thinner compressor 10.

As illustrated in FIG. 7, the output shaft 15 passes through a bearing section 61N of the connecting rod 61C and a bearing section 62N of the connecting rod 62C, and protrudes beyond the opening 33, along the rotation center axis CL, on the side of a second side face section 32 of the case section 23.

As illustrated in FIG. 5 and FIG. 7, an output shaft holding member 91 has a disc portion 91C and a tubular bearing member 91D. The disc portion 91C and the tubular bearing member 91D are formed integrally with each other and are centered around the rotation center axis CL. The disc portion 91C is fixed to the second side face section 32 of the case section 23 in such a way so as to plug the opening 33 of the case section 23. The output shaft 15 is rotatably supported in the bearing member 91D.

An air intake groove section 91E is formed, centered around the rotation center axis CL, in the disc portion 91C. A hood member 92, also referred to as a case, is attachably and removably fixed to the bearing member 91D, centered around the rotation center axis CL, using a screw 92N. The hood member 92 fixes a filter 95 to the disc portion 91C of the output shaft holding member 91. That is, one end section of the ring-like filter 95 abuts into the air intake groove section 91E, and the other end section of the ring-like filter 95 abuts the inner face of the hood member 92. The ring-like filter 95 is concentrically disposed, about the rotation center axis CL, outside the bearing member 91D. So long as the ring-like filter 95 can remove impurities, the material of the ring-like filter 95 is not particularly limited, and may be a porous material, a nonwoven material or the like capable of removing impurities from the raw air that is introduced into the case section 23.

FIG. 10(A) is a perspective-view diagram illustrating the output shaft holding member 91. FIG. 10(B) is a front-view diagram illustrating the shape of the disc portion 91C of the output shaft holding member 91.

As illustrated in FIG. 5, FIG. 7 and FIG. 10, a plurality of air intake holes 99 is arrayed, equidistantly from each other, on a joining portion of the disc portion 91C and the tubular bearing member 91D of the output shaft holding member 91, in such a manner that the air intake holes 99 form a circumference centered around the rotation center axis CL. The plurality of air intake holes 99 makes up a raw air intake section 400. In the example of the figure, 16 air intake holes 99 are equidistantly formed along one same circumference centered around the rotation center axis CL.

FIG. 11 illustrates an example of the cross-sectional shape of the air intake holes 99 of the raw air intake section 400. The air intake holes 99 are formed running through the disc portion 91C of the output shaft holding member 91 in a direction parallel to the rotation center axis CL. Each air intake hole 99 has a first hole section 99A, a second hole section 99B and a tapered section 99T. An inner diameter S1 of the first hole section 99A is set to be greater than an inner diameter S2 of the second hole section 99B. The tapered section 99T is formed between the first hole section 99A and the second hole section 99B. Forming the tapered section 99T allows raw air to be smoothly taken in along arrow directions R3, R4, even when a difference is set between the inner diameter S1 of the first hole section 99A and the inner diameter S2 of the second hole section 99B. In this example, the inner diameter S1 of the first hole section 99A is 1.2 mm, and the inner diameter S2 of the second hole section 99B is 0.5 mm.

The first hole section 99A is formed on the side of an inner face 91G of the disc portion 91C, and the second hole section 99B is formed on the side of an outer face 91H of the disc portion 91C. The introduction channel of raw air (arrow R1, arrow R2, arrow R3) is bent, and is far larger than the inner diameter of the air intake holes 99.

Thus, lower noise is achieved, upon intake of raw air, by causing the raw air to be distributedly taken in via the plurality of raw air intake holes, while securing an effective opening cross-sectional area for raw air intake, by virtue of the configuration wherein the plurality of air intake holes 99 is arrayed along a circumference centered around the rotation center axis CL, as illustrated in FIG. 10, and by virtue of the cross-sectional shape of FIG. 11 of the air intake holes 99.

As illustrated in FIG. 7, raw air passes through the groove section 91E formed between the hood member 92 and the disc portion 91C along arrow R1, and passes from the groove section 91E, along arrow R2, through the filter 95, where dust and dirt are removed; thereafter, the raw air moves along arrow R3 and arrow R4. The air introduction channel (arrow R1, arrow R2, arrow R3) up to air intake holes 99 of the compressor 10 is bent. Setting the air introduction channel to be far larger than the inner diameter of the air intake holes 99, and causing the raw air to be taken into the case section 23 via the plurality of air intake holes 99 allows reducing noise during intake of raw air by, for instance, 4 dB as compared with the case of a large single circular air intake port that is provided in conventional compressors.

As illustrated in FIG. 7, the hood member 92 and the disc portion 91C are preferably accommodated in a space 11P between the first head section 21 and the second head section 22. The raw air intake section 90 of the output shaft 15 is disposed to be accommodated in the space 11P in such a way so as not to protrude beyond the first head section 21 and the second head section 22 in the direction of the rotation center axis CL, and is accommodated within the region formed by the outline portion of the first head section 21 and the outline portion of the second head section 22 in the second side face section 32 of the case section 23. This contributes to achieving a smaller and thinner compressor 10. Also, the driving motor and the raw air intake section 400 can be respectively disposed on the first side face section of the case section, and on the opposite second side face section. This affords a smaller and lighter compressor.

An explanation follows next, with reference to FIG. 12, on a raw air introduction channel 59 and on a discharge channel 79 of compressed air after compression of raw air, in the first head section 21 and the second head section 22 of the compressor 10. In FIG. 12 the contour shape of the compressor 10 is denoted by a two-dot chain line, the raw air introduction channel 59 of the compressor 10 is denoted by a solid line, and the compressed air discharge channel 79 is denoted by a broken line.

The raw air introduction channel 59 denoted by the solid line in FIG. 5 has the first communicating passage 41 communicating with the plurality of air intake holes 99 and the air intake groove section 91E. The first communicating passage 41 communicates with the interior of the first cylinder 61S, at the top, and the interior of the second cylinder 62S, at the bottom. As a result, the raw air 70 can be supplied into the top first cylinder 61S and the bottom second cylinder 62S via the raw air introduction channel 59 denoted by the solid lines.

The compressed air discharge channel 79 of the raw air after compression has the second communicating passage 42 and the discharge port 37, and is connected to the first adsorption barrel 108a and the second adsorption barrel 108b via the duct 6. As a result, the compressed air 80 generated in the top first cylinder 61S and the bottom second cylinder 62S can be supplied to the first adsorption barrel 108a and the second adsorption barrel 108b via the second communicating passage 42 and the duct 6.

An operation example of the oxygen concentrator 1 having the compressor 10 as described above is explained next.

The central processing unit 200 of FIG. 1 issues a command to the motor control unit 201, the motor control unit 201 starts up the driving motor 11 of the compressor 10, and the output shaft 15 of the driving motor 11 illustrated in FIG. 7 and FIG. 9 rotates continuously about the rotation center axis CL. As a result, the first piston 61 of the first head section 21 and the second piston 62 of the second head section 22 illustrated in FIG. 7 reciprocate stably in opposite directions.

In FIG. 7, the second piston 62 is positioned at the bottom dead center in the second cylinder 62S at the same time as when the first piston 61 is positioned at the bottom dead center in the first cylinder 61S. The second piston 62 is positioned at the top dead center in the cylinder 62S at the same time as when the first piston 61 is positioned at the top dead center in the cylinder 61S. As illustrated in FIG. 7, the raw air in the cylinder 61S and the second cylinder 62S are compressed when the first piston 61 and the second piston 623 are at positioned at the top dead center, as in the example illustrated in FIG. 7. Conversely, the raw air is in a suctioned state within the first cylinder 61S and the second cylinder 62S when the first piston 61 and the second piston 623 are positioned at the bottom dead center. That is, the air suction process is performed simultaneously at the second piston 62 and the first piston 61 of the first head section 21; thereafter, a compression process is performed in which compressed air is simultaneously compressed and discharged. The above air suction process and compression process are performed repeatedly.

Upon operation of the first head section 21 and the second head section 22 of the compressor 10, the raw air 70 can be sucked into the top first cylinder 61S and the bottom second cylinder 62S via the plurality of air intake holes 99 and the air intake groove section 91E of the raw air introduction channel 59 denoted by the solid line, and via the first communicating passage 41, as illustrated in FIG. 9.

Upon suction of the raw air 70, impurities can be removed by the separate filter 95 illustrated in FIG. 7. Before impurities accumulate in the filter 95, the latter can be easily cleaned or replaced by removing the hood member 92. This contributes to an easier maintenance of the filter 95.

The hood member 92 covers the periphery of the air intake groove section 91E and the plurality of air intake holes 99. As a result, the hood member 92 allows preventing noise from leaking out directly, from the interior of the case section 23, upon generation of compressed air through suction of raw air as a result of the operation of the pistons through rotation of the output shaft of the driving motor of the compressor. Compressed air can be generated thereby, reliably and with low noise, through suction of raw air towards the pistons. The hood member 92 can function as a noise leak preventing member that prevents leaking, to the exterior, of noise during intake of raw air, as well as of noise from the driving motor 11 itself. Therefore, raw air is taken into the case section 23 quietly while preventing noise from leaking from the compressor 10 directly to the exterior.

In FIG. 9, the compressed air 80 generated in the top first cylinder 61S and the bottom second cylinder 62S can be supplied to the first adsorption barrel 108a and the second adsorption barrel 108b via the second communicating passage 42, the discharge port 37 and the duct 6.

Heat is released upon generation of compressed air through compression of raw air in the compressor 10 of FIG. 1. Accordingly, the compressor 10 is cooled by the blower fan 5 illustrated in FIG. 1. Accordingly, compressed air passes through the duct 6, the three-way switching valves 109a, 109b, and through the adsorbent in the first adsorption barrel 108a and the second adsorption barrel 108b, in which nitrogen is adsorbed and oxygen is separated as a result. Oxygen at a concentration of about 90% or higher thus separated can be stored in the product tank 111.

The oxygen concentration sensor 114 of FIG. 1 detects the oxygen concentration in the product tank 111. The proportional-opening valve 115 opens and closes in response to the oxygen flow rate setting button 308. The oxygen is supplied to the nasal cannula 314 via the sterile filter 119 and the oxygen outlet 7 of the oxygen concentrator 1. As a result, the patient can inhale, for instance, oxygen concentrated to about 90% or more, at a maximum flow rate of 1 L/minute, via the nasal cannula 314.

Figure 14:
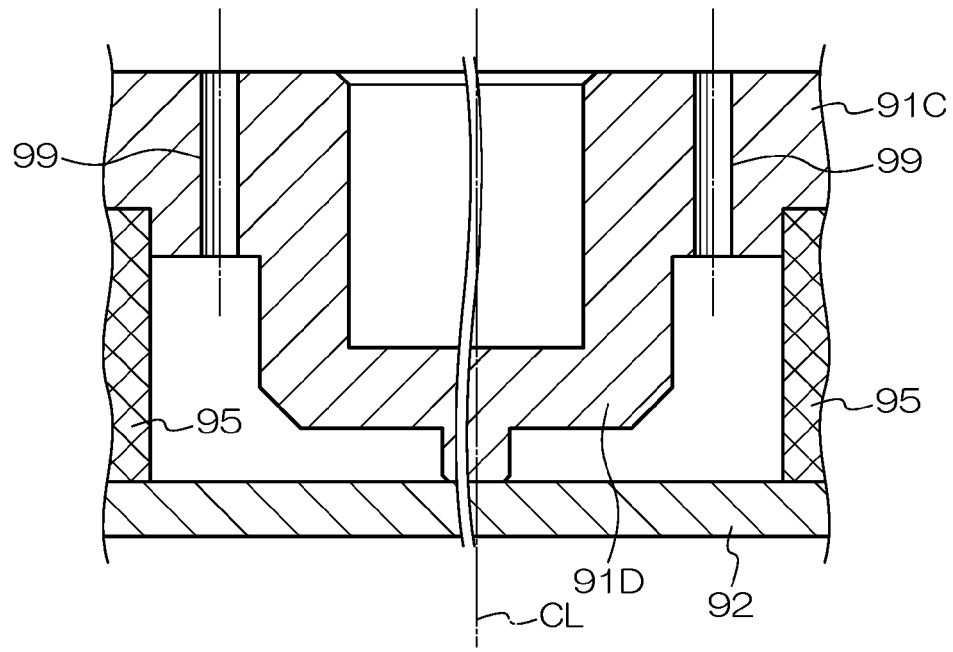
FIG. 14 is a cross-sectional diagram illustrating another embodiment of the air intake hole of the present invention.
Figure 15:
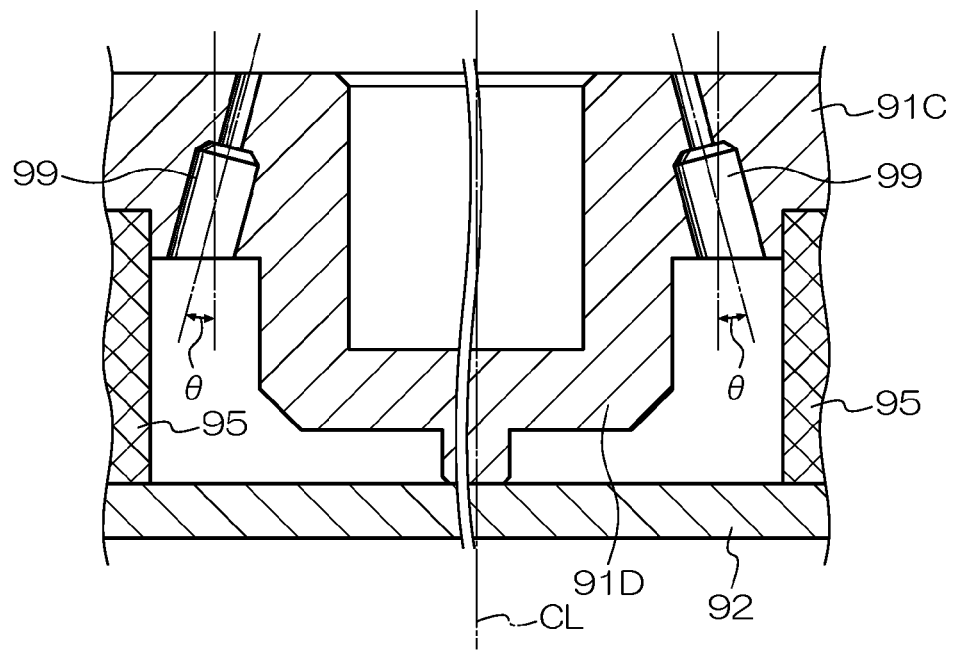
FIG. 15 is a cross-sectional diagram illustrating another embodiment of the air intake hole of the present invention.

An explanation follows next, with reference to FIG. 13 through FIG. 15, on another embodiment of the present invention.

In the embodiment of the present invention illustrated in FIG. 11, the inner diameter of the first hole section 99A of the air intake holes 99 is set to be greater than the inner diameter of the second hole section 99B.

In the embodiment of the present invention illustrated in FIG. 13, by contrast, the inner diameter of a first hole section 99C of the air intake holes 99 may be set to be smaller than the inner diameter of a second hole section 99D. In the embodiment of the present invention illustrated in FIG. 14, the air intake holes 99 may have the same inner diameter along the axial direction.

Alternatively, the air intake holes 99 in the embodiment of the present invention illustrated in FIG. 15 may be formed slanted at an inclination angle θ with respect to the rotation center axis CL. The feature of forming slanting air intake holes 99 can be used in the embodiments of FIG. 11 and FIG. 14.

In all the embodiments of the present invention, the number of air intake holes 99 is not limited to sixteen, and any number of holes may be set. The air intake holes 99 are formed along one circumference, but may be formed along two or more circumferences centered around the rotation center axis CL.

In conventional oxygen concentrators, noise in the compressor includes mainly air intake noise generated at a large air intake port in a case section of the compressor upon introduction of external raw air, and a metallic working noise generated as a result of the opening and closing operation of the valves of a valve member upon introduction of the raw air and discharge of the compressed air. To reduce the air intake noise upon introduction of external raw air, therefore, the compressor must be disposed at a position removed from an air intake opening in the main chassis of the oxygen concentrator. Also, an air intake filter must be provided at the air intake opening of the main chassis, and hence the number of parts increases, and the main body case of the oxygen concentrator becomes inevitably large. It is thus difficult to take radical measures against actual noise. In order to reduce the metallic working noise generated as a result of the opening and closing operation of the valves of a valve member upon introduction of the raw air and discharge of the compressed air, the compressor must be confined within a soundproof box, or must be surrounded by a sound-absorbing material and/or vibration-damping material. In such cases, however, the heat generated by the compressor dissipates less readily, and the main body case of the oxygen concentrator becomes inevitably larger.

In the above-described embodiment of the present invention, by contrast, there is used the compressor 10 having a plurality of raw air intake holes. As a result, noise in the compressor 10 is reduced through reduction of the raw air intake sound upon intake of raw air, the number of parts is reduced, since supplementary components are not necessary, and size and weight of the compressor 10 and the oxygen concentrator 1 are likewise reduced.

Also, using a plastic material as the material of the valve member has the effects of affording a low-noise compressor 10 through reduction of the noise generated by the valve member upon intake of raw air and generation of compressed air, reducing the number of parts, since supplementary components are not necessary, and reducing the size and weight of the compressor 10 and the oxygen concentrator 1.

In the embodiments of the present invention, a compressor that generates compressed air through compression of raw air comprises a case section and a driving motor that is provided in the case section and that has an output shaft; a head section operated by the rotation of the output shaft of the driving motor and that sucks and compresses the raw air to generate thereby the compressed air; and a raw air intake section comprising a plurality of raw air intake holes for taking raw air into the case section and supplying the raw air to the head section. The raw air intake noise as generated during intake of raw air and generation of compressed air can be reduced by causing the raw air to be distributedly taken in via the plurality of raw air intake holes.

The raw air intake holes of the raw air intake section are arrayed centered around the rotation center axis of the output shaft, such that the raw air intake holes are covered by the cylindrical hood member. As a result, the raw air can be distributedly taken into the case section via the raw air intake holes. Also, the raw air intake holes are covered by the cylindrical hood member. This allows preventing the raw air intake holes from being exposed to the exterior, and allows reducing air intake noise.

The driving motor is provided at a first side face section of the case section; and the raw air intake section of the output shaft is provided at a second side face section of the case section, on the opposite side of the first side face section. Also, the driving motor and the raw air intake section can be respectively disposed on the first side face section of the case section, and on the opposite second side face section. This affords a smaller compressor.

Further, a filter that removes impurities from the raw air is provided halfway in the introduction flow path of raw air that is introduced into the raw air intake section from the hood member, and the filter is covered by the hood member. As a result, raw air that is introduced into the raw air intake section via the opening must necessarily pass through the filter. This enables raw air intake in a state where impurities such as dust and dirt have been removed from the raw air, and allows the filter to be covered by the hood member.

The head section of the compressor comprises a first head section provided on the first end section side of the case section and a second head section provided on the second end section side of the case section; the driving motor is accommodated in a region formed by an outline portion of the first head section and an outline portion of the second head section, in the first side face section of the case section; and the hood member and the raw air intake section are accommodated in a region formed by the outline portion of the first head section and the outline portion of the second head section, in a second side face section of the case section. This allows achieving a smaller, lighter and thinner compressor.

An embodiment of the oxygen concentrator of the present invention is an oxygen concentrator provided with a compressor that generates compressed air through compression of raw air, and an adsorption member that holds an adsorbent that adsorbs nitrogen from the compressed air, wherein the compressor comprises a case section and a driving motor that is provided in the case section and that has an output shaft; a head section operated by the rotation of the output shaft of the driving motor and that sucks and compresses the raw air to generate thereby the compressed air; and a raw air intake section comprising a plurality of raw air intake holes for taking raw air into the case section and supplying the raw air to the head section. In the oxygen concentrator of the present invention, as a result, the raw air intake noise as generated during intake of raw air and generation of compressed air can be reduced by causing the raw air to be distributedly taken in via the plurality of raw air intake holes.

In a positive pressure swing adsorption method (PSA) by compressed air alone, only compressed air is fed into the adsorption barrels, where nitrogen is adsorbed. This is advantageous in that the compressor can be smaller and have a simpler structure as compared with vacuum-pressure swing adsorption methods (VPSA) that employ both compressed air and reduced-pressure air.

A synchronous motor is preferably used as the driving motor 11, since in that case the revolutions of the output shaft 15 can be kept constant, and the first head section 21 and the second head section 22 can be driven at stable revolutions, even if the power source voltage fluctuates.

As thus explained, in the present embodiment, in particular, it becomes possible to continuously supply up to 1 L/minute of oxygen concentrated to 90% or above in a small and streamlined transportable oxygen concentrator having reduced power consumption. If a breath synchronization function is operative, it becomes possible to supply up to substantially 3 L/minute of oxygen concentrated to 90% or above.

The present invention is not limited to the above embodiment, and can accommodate various improvements and modifications, and allows for variations without departing from the scope of the claims.

The position of the outer face of the driving motor 11 in FIG. 7 may be identical, in the direction of the rotation center axis CL, to that of the outline portions of the first head section 21 and the second head section 22. Alternatively, the position of the outer face of the driving motor 11 may be lower than that of the outline portion of the first head section 21 and the second head section 22.

The oxygen concentrator is not limited to the portable oxygen concentrator illustrated in the figures, and may be, for instance, a stationary oxygen concentrator. The driving motor of the compressor 10 illustrated in the figures is a synchronous motor, for instance of 1 L class (capable of continuously supplying 1 L/minute of oxygen concentrated to a concentration of 90% or higher). The driving motor that is used is not limited thereto, and may be a motor having a capacity greater than 1 L class, for instance 3 L class (capable of continuously supplying 3 L/minute of oxygen concentrated to a concentration of 90% or higher), or 5 L class (capable of continuously supplying 5 L/minute of oxygen concentrated to a concentration of 90% or higher). Various types of motor, for instance a single-phase AC induction motor, may be used as the driving motor.

The first head section 21 and the second head section 22 are disposed in a horizontally-opposed configuration in which the respective pistons reciprocate in opposite directions, but the first head section 21 and the second head section 22 are not limited thereto, and the two pistons may be disposed in a V configuration.

As illustrated in FIG. 10, the plurality of air intake holes 99 is arrayed along a circumference centered around the rotation center axis CL. However, the holes are not limited thereto, and may be arranged spaced apart from each other along a square shape, a rectangular shape or some other shape.

Explanation of Reference Numerals

1 . . . oxygen concentrator, 2 . . . main chassis (main body cover), 2c . . . air intake port, 3 . . . filter, 4 . . . duct, 6 . . . duct, 10 . . . compressor, 11 . . . driving motor, 15 . . . output shaft, 21 . . . first head section, 22 . . . second head section, 23 . . . case section, 23A . . . first end section (top end section) of case section, 23B . . . second end section (bottom end section) of case section, 59 . . . raw air introduction channel, 70 . . . raw air, 71 . . . compressed air, 79 . . . compressed air discharge channel, 90 . . . raw air intake section of output shaft, 90S . . . screw, 91 . . . output shaft holding member, 91D . . . tubular bearing member, 91E . . . air intake groove section, 92 . . . hood member, 93 . . . hood case, 94 . . . cover member, 95 . . . filter, 99 . . . air intake holes, 108a . . . first adsorption barrel (adsorption member), 108b . . . second adsorption barrel (adsorption member), 194 . . . reed valve member (example of a valve member), 194A . . . reed valve (example of a first valve body), 194B . . . reed valve (example of a second valve body), 400 . . . raw air intake section comprising a plurality of air intake holes

The invention claimed is:

1. An oxygen concentrator provided with a compressor that generates compressed air by compressing raw air, and an adsorption member that holds an adsorbent that adsorbs nitrogen from the compressed air, wherein
the compressor has:
a case section;
a driving motor that is provided in the case section and that has an output shaft;
a head section operated by rotation of the output shaft of the driving motor and that sucks and compresses the raw air to generate thereby the compressed air; and
a raw air intake section formed of a plurality of raw air intake holes for taking the raw air into the case section and supplying the raw air to the head section;
the raw air intake holes of the raw air intake section are arrayed along a circumference centered around a rotation center axis of the output shaft, and the raw air intake holes are covered by a cylindrical hood member; and
wherein each of the raw air intake holes has a first hole section, a second hole section and a tapered section along in the direction of a flow path of introducing the raw air, an inner diameter of the first hole section is set to be greater than an inner diameter of the second hole section, the tapered section is formed between the first hole section and the second hole section.

2. The oxygen concentrator according to claim 1, wherein the driving motor is provided at a first side face section of the case section; and the raw air intake section is provided at a second side face section on an opposite side to the first side face section of the case section.

3. The oxygen concentrator according to claim 2, wherein a filter that removes impurities from the raw air is provided halfway in a flow path of introducing the raw air that is introduced into the raw air intake section from the hood member, and the filter is covered by the hood member.

4. The oxygen concentrator according to claim 3, wherein the head section of the compressor has a first head section provided on a first end section side of the case section and a second head section provided on a second end section side of the case section;
the driving motor is accommodated in a region formed by an outline portion of the first head section and an outline portion of the second head section, in the first side face section of the case section; and the hood member and the raw air intake section are accommodated in a region formed by the outline portion of the first head section and the outline portion of the second head section, in the second side face section of the case section.

5. The oxygen concentrator according to claim 1, wherein a filter that removes impurities from the raw air is provided halfway in a flow path of introducing the raw air that is introduced into the raw air intake section from the hood member, and the filter is covered by the hood member.

6. The oxygen concentrator according to claim 5, wherein the head section of the compressor has a first head section provided on a first end section side of the case section and a second head section provided on a second end section side of the case section;
the driving motor is accommodated in a region formed by an outline portion of the first head section and an outline portion of the second head section, in the first side face section of the case section; and the hood member and the raw air intake section are accommodated in a region formed by the outline portion of the first head section and the outline portion of the second head section, in the second side face section of the case section.

7. An oxygen concentrator, the oxygen concentrator comprising:
a compressor configured to generate compressed air by compressing raw air, the compressor comprising:
a case section;
a driving motor that is provided in the case section and having an output shaft;
a head section configured to operate by rotation of the output shaft of the driving motor and configured to generate the compressed air; and
a raw air intake section formed of a plurality of raw air intake holes for taking the raw air into the case section and supplying the raw air to the head section, the raw air intake holes of the raw air intake section are arranged around a rotation center axis of the output shaft, each of the raw air intake holes having a first hole section, a second hole section and a tapered section along in the direction of a flow path of introducing the raw air, wherein an inner diameter of the first hole section is greater than an inner diameter of the second hole section, and the tapered section is formed between the first hole section and the second hole section.

8. The oxygen concentrator according to claim 7, comprising:
a cylindrical hood member, wherein the raw air intake holes are covered by the cylindrical hood member.

9. The oxygen concentrator according to claim 8, wherein the driving motor is provided at a first side face section of the case section, and the raw air intake section is provided at a second side face section on an opposite side to the first side face section of the case section.

10. The oxygen concentrator according to claim 9, wherein a filter that removes impurities from the raw air is provided halfway in a flow path of introducing the raw air that is introduced into the raw air intake section from the hood member, and the filter is covered by the hood member.

11. The oxygen concentrator according to claim 10, wherein
the head section of the compressor has a first head section provided on a first end section side of the case section and a second head section provided on a second end section side of the case section;
the driving motor is accommodated in a region formed by an outline portion of the first head section and an outline portion of the second head section, in the first side face section of the case section; and the hood member and the raw air intake section are accommodated in a region formed by the outline portion of the first head section and the outline portion of the second head section, in the second side face section of the case section.

12. The oxygen concentrator according to claim 8, comprising:
a filter configured to remove impurities from the raw air, and wherein the filter is provided halfway in a flow path of introducing the raw air that is introduced into the raw air intake section from the hood member, and the filter is covered by the hood member.

13. The oxygen concentrator according to claim 12, wherein
the head section of the compressor has a first head section provided on a first end section side of the case section and a second head section provided on a second end section side of the case section;
the driving motor is accommodated in a region formed by an outline portion of the first head section and an outline portion of the second head section, in the first side face section of the case section; and the hood member and the raw air intake section are accommodated in a region formed by the outline portion of the first head section and the outline portion of the second head section, in the second side face section of the case section.

14. The oxygen concentrator according to claim 7, wherein the driving motor is provided at a first side face section of the case section, and the raw air intake section is provided at a second side face section on an opposite side to the first side face section of the case section.

15. The oxygen concentrator according to claim 14, comprising:
a filter configured to remove impurities from the raw air, and wherein the filter is provided halfway in a flow path of introducing the raw air that is introduced into the raw air intake section from the hood member, and the filter is covered by a hood member.

16. The oxygen concentrator according to claim 15, wherein
the head section of the compressor has a first head section provided on a first end section side of the case section and a second head section provided on a second end section side of the case section;
the driving motor is accommodated in a region formed by an outline portion of the first head section and an outline portion of the second head section, in the first side face section of the case section; and the hood member and the raw air intake section are accommodated in a region formed by the outline portion of the first head section and the outline portion of the second head section, in the second side face section of the case section.

17. The oxygen concentrator according to claim 7, comprising:
an adsorbent, which absorbs nitrogen from the compressed air.

* * * * *